United States Patent
Rangappa et al.

(10) Patent No.: US 9,604,974 B2
(45) Date of Patent: Mar. 28, 2017

(54) COMPOUNDS AS MODULATOR OF JAK-STAT PATHWAY, METHODS AND APPLICATIONS THEREOF

(71) Applicants: UNIVERSITY OF MYSORE, Mysore (IN); NATIONAL UNIVERSITY OF SINGAPORE, Singapore (SG); BANGALORE UNIVERSITY, Bengaluru (IN); CAMBRIDGE ENTERPRISE LTD, Cambridge (GB)

(72) Inventors: Kanchugarakoppal Subbegowda Rangappa, Mysore (IN); Basappa, Bangalore (IN); Chakrabhavi Dhananjaya Mohan, Mysore (IN); Shobith Rangappa, Sapporo (JP); Hanumantharayappa Bharathkumar, Bangalore (IN); Gautam Sethi, Singapore (SG); Andreas Bender, Cambridge (GB); Peter Edward Lobie, Singapore (SG); Kam Man Hui, Singapore (SG); Alan Prem Kumar, Singapore (SG); Vijay Kumar Pandey, Singapore (SG); Julian Fuchs, Cambridge (GB); Muthu Kumaraswamy Shanmugam, Singapore (SG); Krishna Bulusu, Cambridge (GB); Xiaoyun Dai, Singapore (SG); Feng Li, Singapore (SG); Amudha Deivasigamani, Singapore (SG)

(73) Assignees: UNIVERSITY OF MYSORE, Karnataka (IN); NATIONAL UNIVERSITY OF SINGPORE, Singapore (SG); BANGALORE UNIVERSITY, Karnataka (IN); CAMBRIDGE ENTERPRISE LTD, Cambridge (GB)

( * ) Notice: Subject to any disclaimer, the term of this patent is extended or adjusted under 35 U.S.C. 154(b) by 0 days.

(21) Appl. No.: 15/004,114

(22) Filed: Jan. 22, 2016

(65) Prior Publication Data
US 2016/0214968 A1   Jul. 28, 2016

(30) Foreign Application Priority Data

Jan. 22, 2015  (IN) .............................. 324/CHE/2015

(51) Int. Cl.
*C07D 413/04*    (2006.01)
*C07D 265/16*    (2006.01)

(52) U.S. Cl.
CPC ......... *C07D 413/04* (2013.01); *C07D 265/16* (2013.01)

(58) Field of Classification Search
CPC ........................... C07D 413/04; C07D 265/16
USPC ......................................... 544/71; 514/228.8
See application file for complete search history.

(56) References Cited

FOREIGN PATENT DOCUMENTS

JP      2007254391 A   *  10/2007

* cited by examiner

*Primary Examiner* — Kahsay Habte
(74) *Attorney, Agent, or Firm* — Hamre, Schumann, Mueller & Larson, P.C.

(57) ABSTRACT

The present disclosure relates to compound of structural Formula I and a method for preparing said compounds. The disclosure further relates to a method of employing the Formula I compounds for modulation of Janus kinase-Signal Transducer and Activator of Transcription (JAK-STAT) pathway in cancer cells, and the corresponding use of compound of Formula I as anti-cancer agents.

Figure 1:
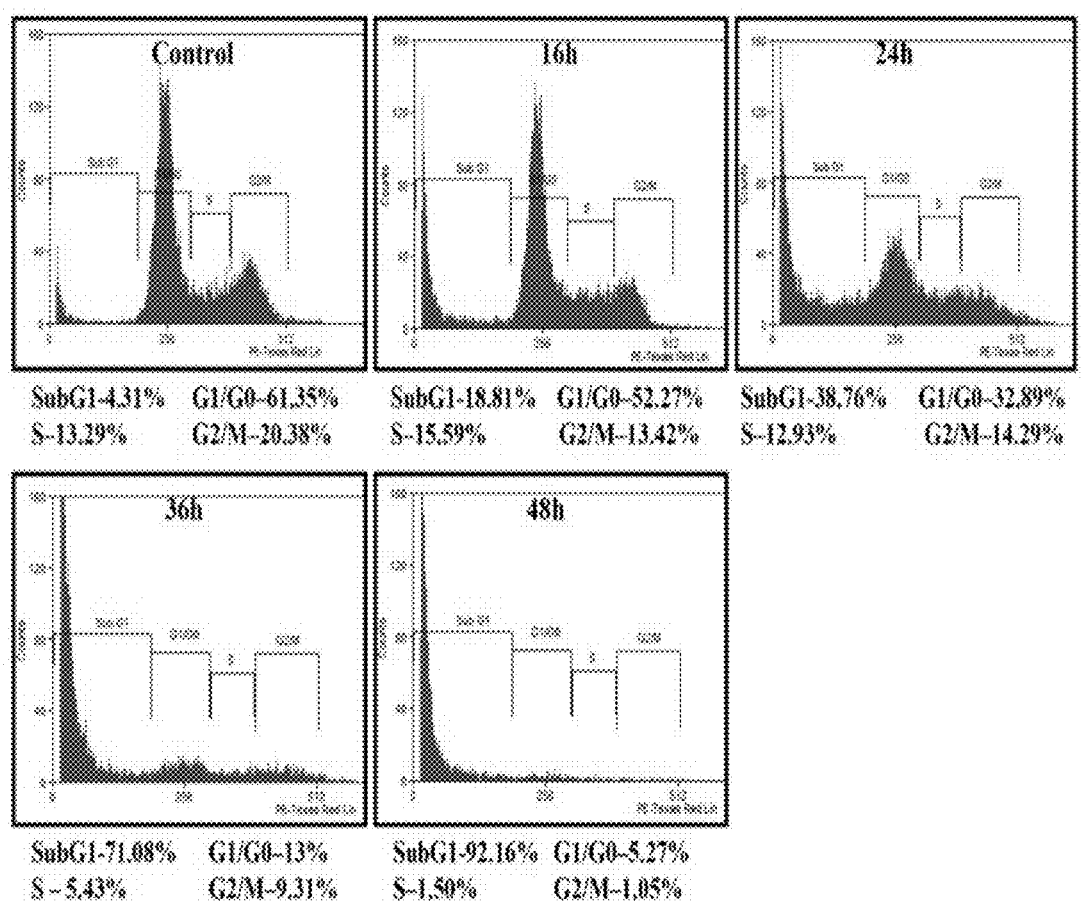

18 Claims, 8 Drawing Sheets
(6 of 8 Drawing Sheet(s) Filed in Color)

COMPOUNDS AS MODULATOR OF JAK-STAT PATHWAY, METHODS AND APPLICATIONS THEREOF

TECHNICAL FIELD

The present disclosure is in the field of biological chemistry. The disclosure relates to compounds, which are potent modulators of Janus kinase-Signal Transducer and Activator of Transcription 3 (JAK-STAT3) pathway in cancer cells. In particular, said compounds of the present disclosure act as inhibitors/abrogators of JAK-STAT3 pathway, and are employed as anti-cancer agents.

BACKGROUND AND PRIOR ART OF THE DISCLOSURE

Cancer, also known as a malignant tumor or malignant neoplasm, is a group of diseases involving abnormal cell growth with the potential to invade or spread to other parts of the body. In particular, hepatocellular carcinoma (HCC) is a fatal liver cancer affecting 600,000 people worldwide annually, and it ranks third in terms of global cancer mortality. The development and progression of HCC is largely associated with endemic hepatitis B or hepatitis C virus infection, alcoholic hepatitis, non-alcoholic steatohepatitis, hemochromatosis, obesity and consumption of aflatoxin B1. Surgical therapies including liver resection, liver transplantation as well as non-surgical therapies such as embolization, systemic chemotherapy and radiation therapy are currently available for the treatment/prognosis of HCC.

Signal Transducer and Activator of Transcription 3 (STAT3) is an inducible transcription factor/protein present in the cytoplasm of most cell types, and it is involved in extracellular signal transduction to the nucleus by cytokines of the IL-6 family, epidermal and platelet-derived growth factors. Thus, STAT3 governs differentiation, proliferation and survival of cells. Further, in a tumor, STAT3 is involved in its proliferation, development, survival, angiogenesis, metastasis and evasion. Activation of STAT3 is also known to transmit various survival signals by promoting the expression of genes involved in cell cycle progression (cyclin D1), angiogenesis (VEGF, HIF-1α), cell migration (MMP-2/9), immune evasion (RANTES) and anti-apoptotic genes (Bcl2, Bcl-xL, survivin). JAK1, JAK2, JAK3 and Tyrosine kinase 2 (TYK2) are the upstream kinases which phosphorylate different STAT proteins involved in different functions. Structurally, the activation of Janus kinase (JAK) and c-Src kinase leads to the phosphorylation of tyrosine 705 and homodimerization of STAT3, followed by its nuclear translocation to transcribe the target genes. Constitutive activation of STAT3 is observed in more than 15 types of solid and haematological tumors, including hepatocellular carcinoma, leukemia, lymphoma, prostate cancer, breast cancer, ovarian cancer and multiple myeloma. To summarize, STAT3 plays a critical role in progression of cancer (such as hepatocellular carcinoma).

Many compounds have been studied extensively for modulation of cancer-associated biological pathways and are shown to have anti-cancer activity in various tumor models. However, the compounds of prior art possess numerous drawbacks such as complex synthesis procedures, toxicity to normal cells, lack of stability, lack of improved/desired anti-cancer efficacy, and so on.

Thus, there is a necessity to develop better and efficient compounds/therapies for managing cancer. The present disclosure aims at providing such compounds which possess significantly improved anti-cancer activity.

STATEMENT OF THE DISCLOSURE

Accordingly, the present disclosure relates to a compound of Formula I

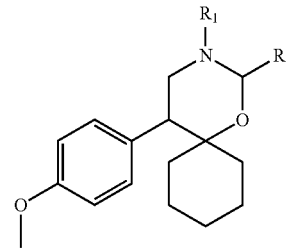

Formula I where, 'R' is selected from a group consisting of indole, imidazole, phenyl, chromene-4-one and dihydrobenzofuran, and wherein said 'R' is optionally substituted, '$R_1$' is hydrogen or benzyl; and wherein the benzyl is optionally substituted, or its tautomers, isomers, analogs, derivatives or salts thereof;

a method for preparing a compound of Formula I,

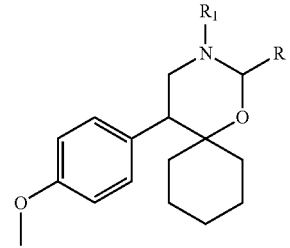

Formula I where, 'R' is selected from a group consisting of indole, imidazole, phenyl, chromene-4-one and dihydrobenzofuran, and wherein said 'R' is optionally substituted, '$R_1$' is hydrogen or benzyl, and wherein the benzyl is optionally substituted, or its tautomers, isomers, analogs, derivatives or salts thereof.

said method comprising steps of:
a) reacting amino alcohol with an aldehyde in presence of a base to obtain the compound of Formula I wherein '$R_1$' is hydrogen, 'R' is selected from a group consisting of indole, imidazole, phenyl, chromene-4-one and dihydrobenzofuran, and said 'R' is optionally substituted, and
b) optionally, reacting the compound of Formula I of step (a) with a substituted benzyl halide to obtain the compound of Formula I, wherein 'R' is phenyl which is optionally substituted, and '$R_1$' is benzyl which is optionally substituted;

and, a method of inhibiting a protein selected from a group comprising tyrosine kinase, Signal Transducer and Activator of Transcription (STAT) and a combination thereof in a cancer cell, said method comprising act of contacting the compound of claim 1 with the cancer cell for inhibiting the protein.

BRIEF DESCRIPTION OF ACCOMPANYING FIGURES

The patent or application file contains at least one drawing executed in color. Copies of this patent or patent application publication with color drawings will be provided by the Office upon request and payment of the necessary fee. In order that the disclosure may be readily understood and put into practical effect, reference will now be made to exemplary embodiments as illustrated with reference to the accompanying figures. The figures together with a detailed description below, are incorporated in and form part of the specification, and serve to further illustrate the embodiments and explain various principles and advantages, in accordance with the present disclosure where:

FIG. 1 depicts the accumulation of HepG2 cells in SubG1 phase caused by Compound 1 (CIMO). HepG2 cells ($5 \times 10^5$/mL) are treated with 10 μMol/L CIMO for indicated time points, after which the cells are washed, fixed, stained with PI, and analyzed for DNA content by flow cytometry.

Figure 2:
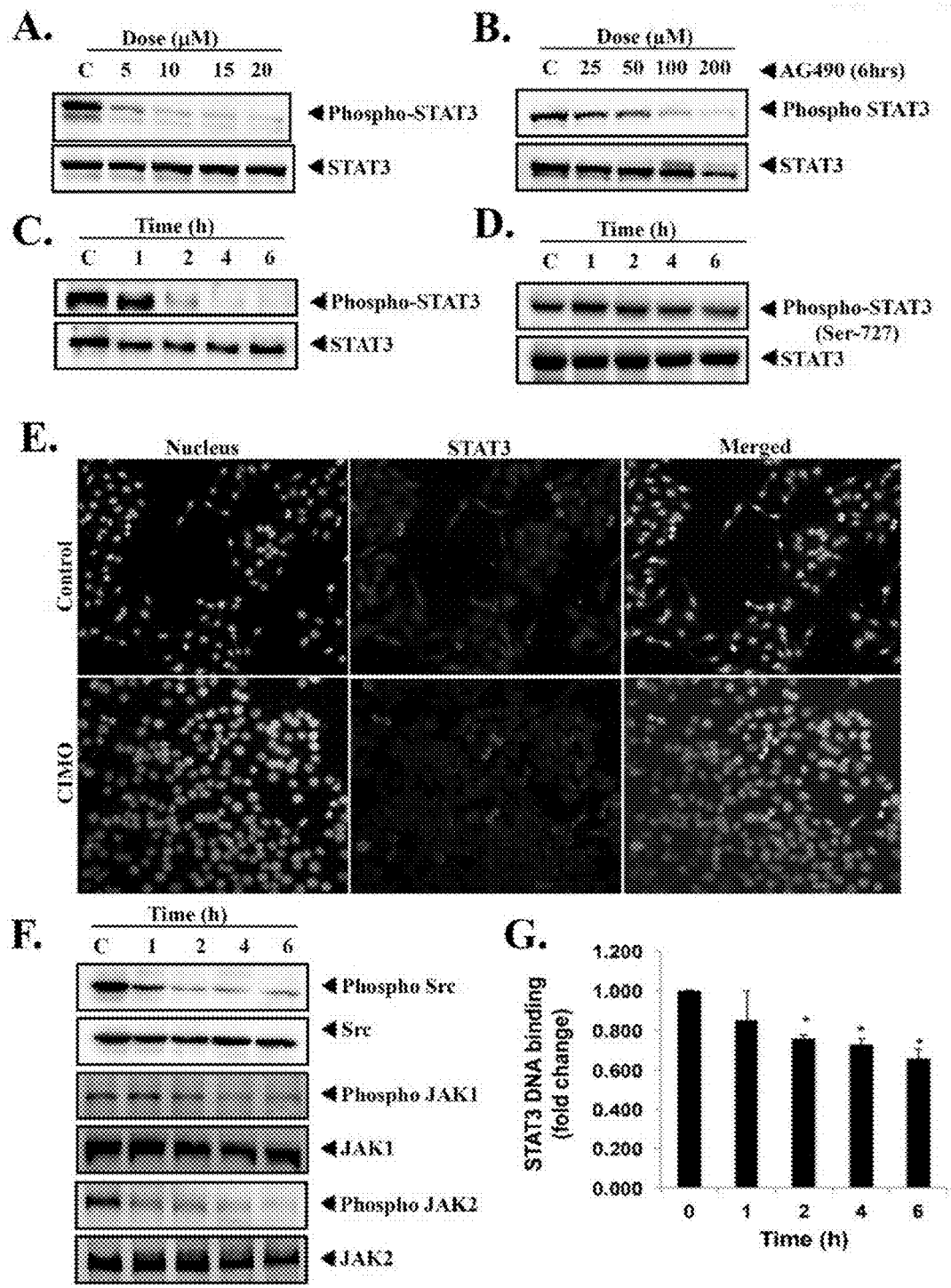

FIG. 2 depicts the suppression of phospho-STAT3 by compound 1 (CIMO) in a dose dependent manner [A]. HepG2 cells ($5 \times 10^5$/mL) are treated with the indicated concentrations of CIMO for 6 hours, after which whole-cell extracts are prepared and resolved on SDS-PAGE gel, electrotransferred onto nitrocellulose membrane, and probed for phospho-STAT3. The same blot is stripped and reprobed with STAT3 antibody to verify equal protein loading. [B] shows the suppression of phospho-STAT3 by AG490 in a dose-dependent manner. HepG2 cells ($5 \times 10^5$/mL) are treated with the indicated concentrations of AG490 for about 6 hours, after which Western Blotting is done as described for [A]. [C] depicts the suppression of phospho-STAT3 levels by Compound 1 (CIMO) in a time-dependent manner. HepG2 cells ($5 \times 10^5$/mL) are treated with 10 μMol/L CIMO for the indicated times, after which Western blotting is done as described for [A]. [D] depicts that compound 1 (CIMO) has no effect on phospho-STAT3 (Ser-727) and STAT3 protein expression. HepG2 cells ($5 \times 10^5$/mL) are treated with 10 μMol/L CIMO for the indicated times, after which Western Blotting is done as described for [A] and membrane is probed using antibodies against phospho-STAT3 (Ser-727) and STAT3. [E] shows the inhibition of translocation of STAT3 to the nucleus by Compound 1 (CIMO). HepG2 cells ($1 \times 10^5$/mL) are incubated with or without 10 μMol/L CIMO for about 6 hours and then analyzed for the intracellular distribution of STAT3 by immunocytochemistry. The same slides are counterstained for nuclei with Hoechst (50 ng/mL) for about 5 minutes and analyzed under an fluorescencemicroscope. [F] shows the suppression of phospho-Src, phospho-JAK1 and phospho-JAK2 levels by Compound 1 (CIMO) in a time-dependent manner. HepG2 cells ($5 \times 10^5$/mL) are treated with 10 μMol/L CIMO, after which whole-cell extracts are prepared, resolved in SDS-PAGE, electrotransferred onto nitrocellulose membrane, and probed with phospho-Src, phospho-JAK1 and phospho-JAK2 antibodies. The same blots are stripped and reprobed with Src, JAK1 and JAK2 antibodies to verify equal protein loading. [G] depicts the suppression of STAT3 DNA binding ability by Compound 1 (CIMO) in HepG2 cells. HepG2 cells are treated with 10 μMol/L CIMO for the indicated time, nuclear extracts are prepared, and 5 μg of the nuclear extract protein is used for ELISA-based DNA-binding assay.

Figure 3:
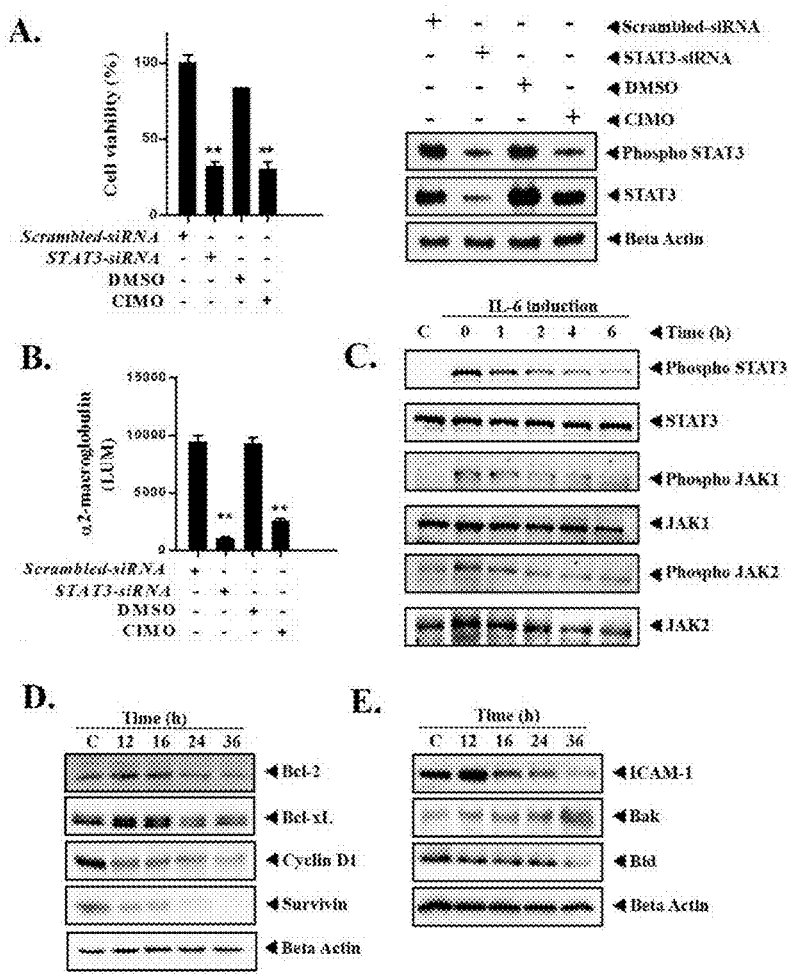

FIG. 3 depicts comparative study of cell viability between STAT3-siRNA transfected and Compound 1 (CIMO) treated HepG2 cells [A]. Correspondingly, Western Blot analysis is used to assess the levels of phospho-STAT3 and STAT3 in HepG2 cells with siRNA-mediated depletion STAT3 expression and on exposure to 4 μM CIMO. Whole cell extract is prepared and resolved on SDS-PAGE gel, electrotransferred onto nitrocellulose membrane, and probed for phospho-STAT3 and the same blot is stripped and reprobed with STAT3 antibody and Beta actin to verify equal protein loading. [B] showcases the modulation of STAT3 mediated transcription, α2-M promoter activity by Compound 1 (CIMO) in HepG2 cells. [C] depicts the inhibition of IL-6-induced phosphorylation of STAT3, JAK1 and JAK2 by Compound 1 (CIMO). Hep3B cells ($5 \times 10^5$/mL) are treated with 10 μMol/L CIMO for the indicated times and then stimulated with IL-6 (10 ng/mL) for about 15 minutes. Whole-cell extracts are then prepared, resolved on SDS-PAGE gel, electrotransferred onto nitrocellulose membrane and probed with phospho-STAT3, phospho-JAK1 and phospho-JAK2 antibodies. The same blot is stripped and reprobed with STAT3, JAK1 and JAK2 antibody to verify equal protein loading. [D] and [E], showcases the suppression of STAT3 regulated gene products involved in cell proliferation and survival by Compound 1 (CIMO). HepG2 cells ($5 \times 10^5$/mL) are treated with 10 μMol/L of CIMO for indicated time intervals, after which whole-cell extract are prepared, resolved on SDS-PAGE gel, electrotransferred onto nitrocellulose membrane, and membrane sliced according to molecular weight and probed against Bcl-2, Cyclin D1, Survivin, Bak, ICAM-1, Bcl-xL and Bid. The same blot is stripped and reprobed with Beta actin antibody to verify equal protein loading.

Figure 4:
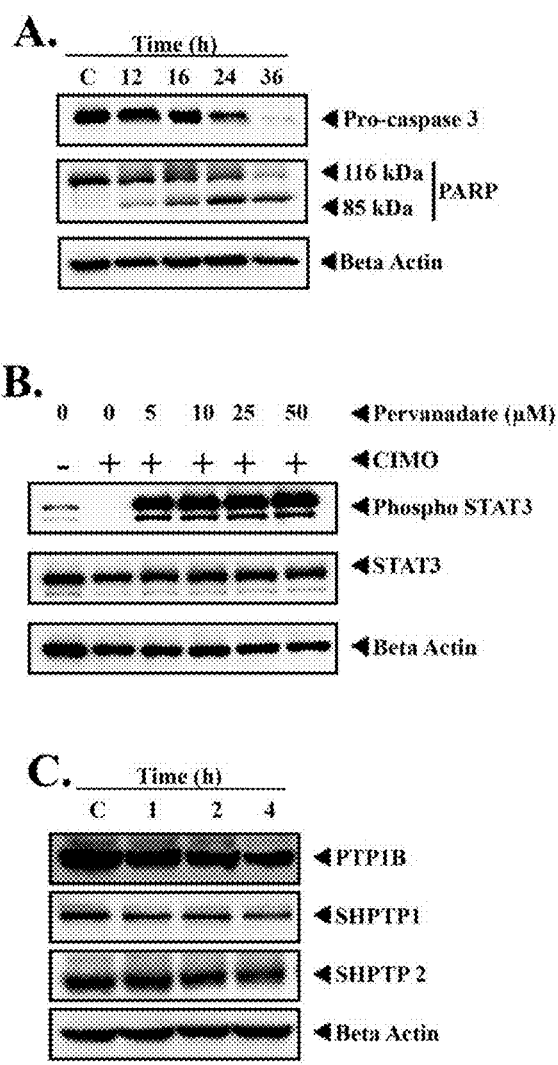

FIG. 4 depicts activation of caspase-3 and induction of apoptosis by Compound 1 (CIMO) [A]. HepG2 cells ($5 \times 10^5$/mL) are treated with 10 μMol/L CIMO for the indicated times, whole-cell extracts are prepared, separated on SDS-PAGE, and subjected to Western Blotting against caspase-3 and PARP antibody. The same blot is stripped and reprobed with Beta actin antibody to show equal protein loading. [B] Tyrosine phosphatase inhibitor-sodium pervanadate reverses the inhibitory effect of Compound 1 (CIMO) on phospho-STAT3. HepG2 cells ($5 \times 10^5$/mL) are treated with the indicated concentrations of sodium pervanadate and 10 μMol/L CIMO for about 4 hours, after which whole-cell extracts are prepared, resolved on SDS-PAGE gel, electrotransferred onto nitrocellulose membrane, and probed for phospho-STAT3 and STAT3. [C] illustrates the inhibitory activity of Compound 1 (CIMO) on phospho-STAT3 mediated by protein tyrosine phosphatase. HepG2 cells ($5 \times 10^5$/mL) are treated with 10 μMol/L CIMO for the indicated times, whole-cell extracts are prepared, separated on SDS-PAGE, and subjected to Western Blotting against PTP1B, SHPTP1 and SHPTP2 antibodies and the same blot is stripped and reprobed with Beta actin antibody to show equal protein loading.

Figure 5:
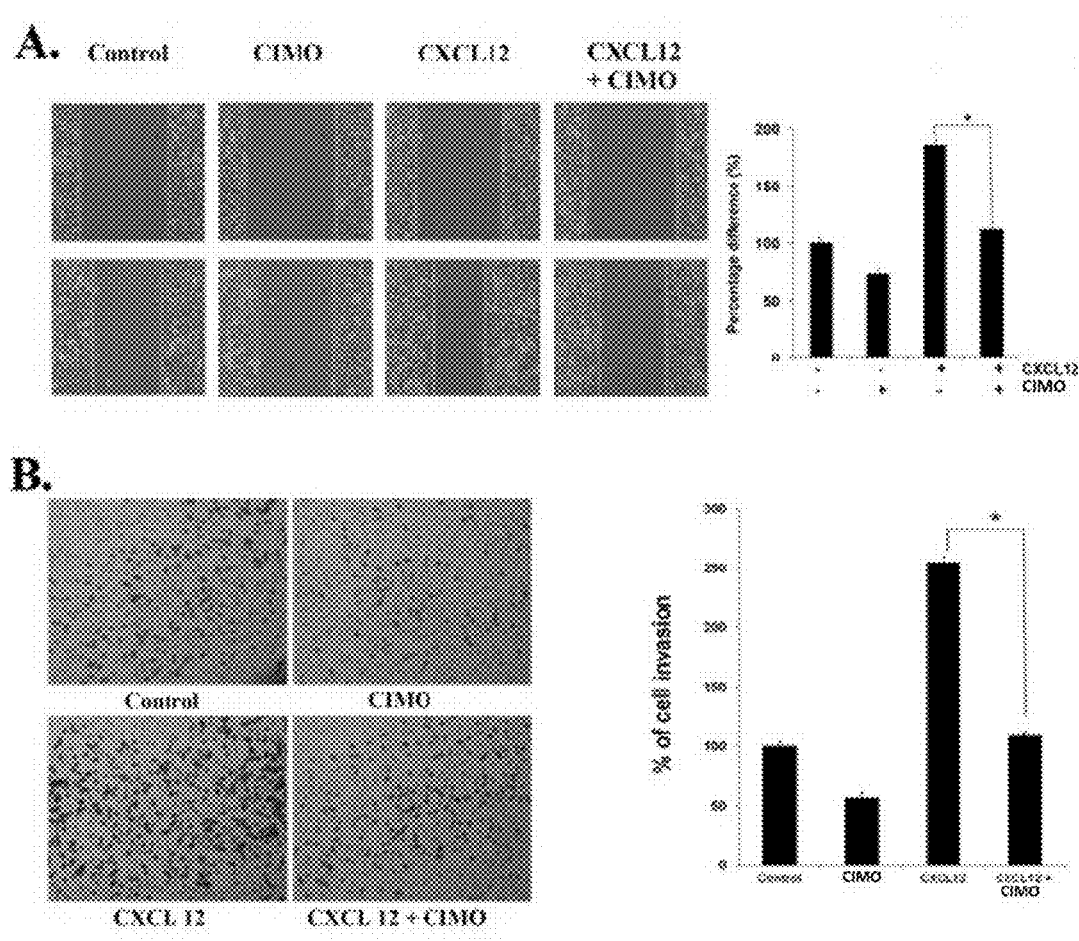

FIG. 5 depicts inhibition of cell migration by Compound 1 (CIMO) [A]. 70 μl HepG2 cells ($5 \times 10^5$/mL) are seeded into each compartments of culture insert and insert is removed after about 12 hours. Width of the wound is measured initially and incubation is carried out with and without CIMO (5 μM, for about 8 hours) and CXCL12 (100 ng/mL, for about 24 hours). [B] Inhibition of cell invasion by Compound 1 (CIMO). HepG2 ($2 \times 10^5$) cells are seeded in the top chamber of BD BioCoat™ Matrigel™. After preincubation with or without 5 μMol/L CIMO for about 8 hours, transwell chambers are placed into the wells of a 24-well plate which contains either only basal medium or basal medium with CXCL12 (100 ng/mL) for about 24 hours. After incubation, the chambers are assessed for cell invasion by staining with crystal violet.

Figure 6:
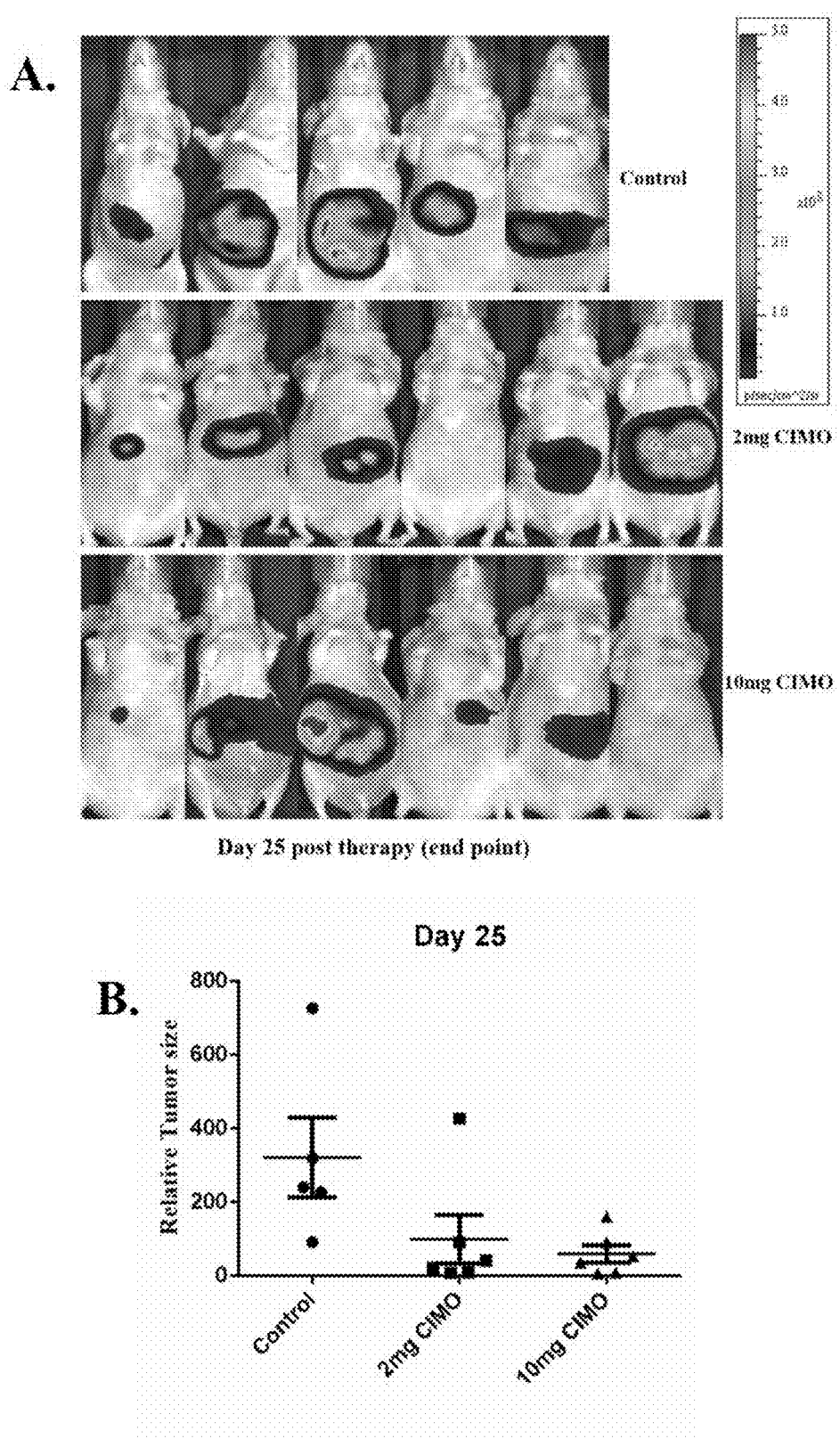

FIG. 6 showcases inhibition of the growth of human hepatocellular carcinoma (HCC) in vivo by CIMO. [A] Representative images of mice from bioluminescent imaging. [B] Relative tumor burden in athymic mice bearing orthotopically implanted Huh 7-Luc2 tumors treated with vehicles alone (n=5), 2 mg/kg (n=6) or 10 mg/kg (n=6) of CIMO. Points, mean; bars, SE. *=p<0.05 (unpaired t-test).

Figure 7:
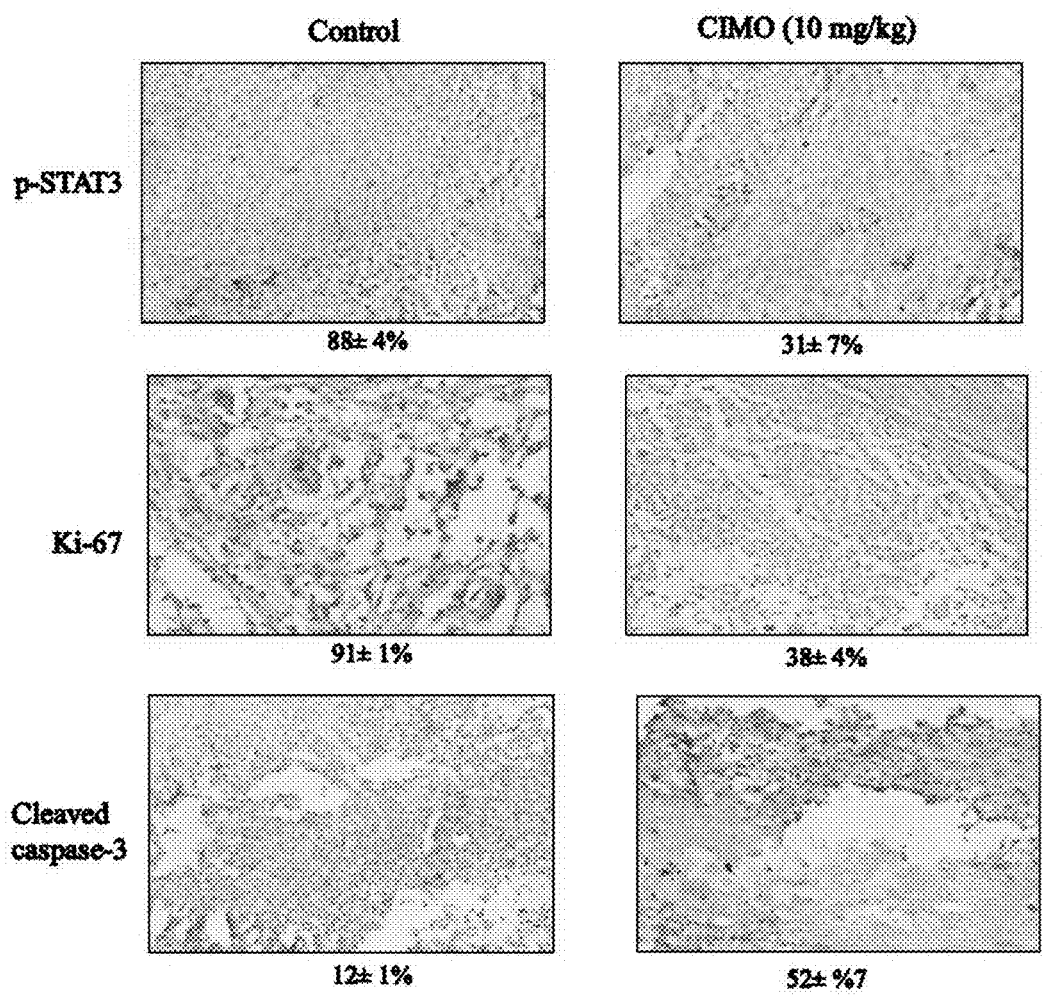

FIG. 7 depicts immunohistochemical analysis of phospho-STAT3, Ki-67, and caspase-3 showcasing the inhibition in expression of phospho-STAT3, and Ki-67 and increased levels of cleaved caspase-3 expression in Compound 1 (CIMO) treated samples as compared with control group. Percentage indicates positive staining for the given biomarker. The photographs were taken at the magnification of 40×.

Figure 8:
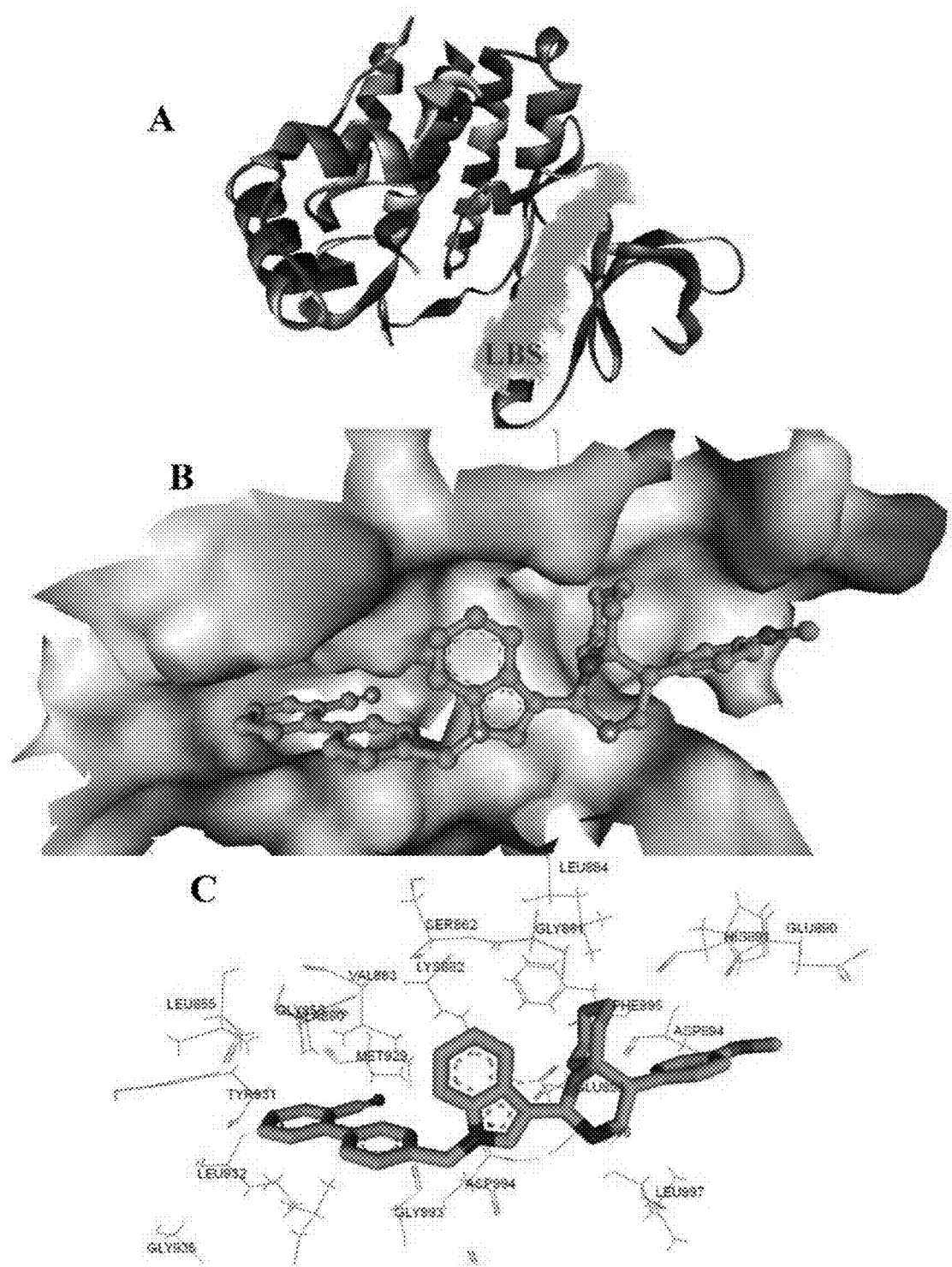

FIG. 8 relates to bioinformatics approach of CIMO interaction towards the kinase domain of JAK2. [A] The ribbon diagram of the monomer of the JAK2 and its ligand binding site (LBS) of kinase domain (green color) is presented. [B] Surface view of JAK2 and the bound CIMO at the LBS region is presented. [C] Interaction map of LBS domain of JAK2 that interacts with CIMO. The labeled key amino acids are represented as a line model with the carbon atom as black, and other atoms in their parent colors. The binding of CIMO, whose carbon atom is colour in green and other atoms with their parent color.

DETAILED DESCRIPTION OF THE DISCLOSURE

The present disclosure relates to a compound of Formula I

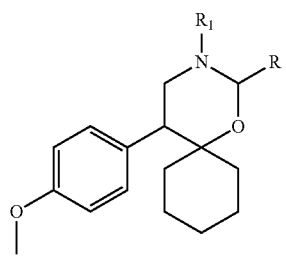

Formula I where, 'R' is selected from a group consisting of indole, imidazole, phenyl, chromene-4-one and dihydrobenzofuran, and wherein said 'R' is optionally substituted,
'R$_1$' is hydrogen or benzyl; and wherein the benzyl is optionally substituted,
or its tautomers, isomers, analogs, derivatives or salts thereof;

In an embodiment of the present disclosure, the compound of Formula I is selected from a group comprising:
2-(1-(4-(2-cyanophenyl)1-benzyl-1H-indol-3-yl)-5-(4-methoxy-phenyl)-1-oxa-3-aza spiro(5,5) undecane;
2-(2-butyl-5-chloro-3H-imidazol-4-yl)-5-(4-methoxy-phenyl)-1-oxa-3-aza spiro(5,5) undecane;
2-(2-butyl-5-chloro-3-(4-(2-cyanophenyl)1-benzyl)-imidazol-4-yl)-5-(4-methoxy-phenyl)-1-oxa-3-aza spiro(5,5) undecane;
2-(4-Bromophenyl)-5-(4-methoxy-phenyl)-1-oxa-3-aza spiro(5,5) undecane;
2-(2-phenylindyl)-5-(4-methoxy-phenyl)-1-oxa-3-aza spiro (5,5) undecane;
2-(indyl)-5-(4-methoxy-phenyl)-1-oxa-3-aza spiro(5,5) undecane;
2-(2-butyl-5-chloro-3-(4-benzyloxy-1-benzyl)-imidazol-4-yl)-5-(4-methoxy-phenyl)-1-oxa-3-aza spiro(5,5)undecane;
3-[5-(4-Methoxy-phenyl)-1-oxa-3-aza-spiro[5.5]undec-2-yl]-chromen-4-one;
2-(2-methyl indyl)-5-(4-methoxy-phenyl)-1-oxa-3-aza spiro (5,5) undecane;
2-(2,6-dichlorophenyl)-5-(4-methoxy-phenyl)-1-oxa-3-aza spiro(5,5) undecane;
2-(2,3-Dihydro-benzofuran-5-yl)-5-(4-methoxy-phenyl)-1-oxa-3-aza-spiro[5,5]undecane;
2-(2,6-dichlorophenyl)-5-(4-methoxy-phenyl)-1-oxa-3-(4-(2-cyanophenyl)benzyl azaspiro(5,5) undecane;
and
2-(4-dimethyl amino phenyl)-5-(4-methoxy-phenyl)-1-oxa-3-aza spiro(5,5) undecane.

In another embodiment of the present disclosure, the compound of Formula I is crystalline and has a melting point ranging from about 55° C. to about 160° C.

In yet another embodiment of the present disclosure, the compound of Formula I is soluble in solvent selected from a group comprising DMSO, CDCl3, methanol, DMF, ethanol and combinations thereof.

The present disclosure further relates to a method for preparing a compound of Formula I,

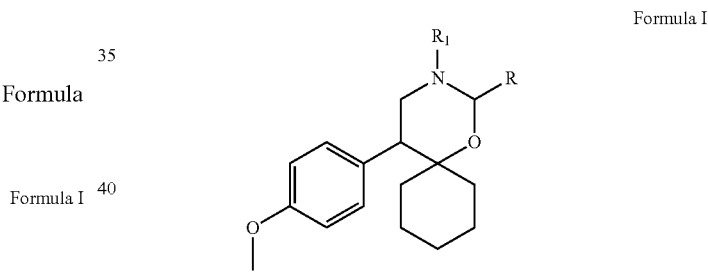

Formula I where, 'R' is selected from a group consisting of indole, imidazole, phenyl, chromene-4-one and dihydrobenzofuran, and wherein said 'R' is optionally substituted,
'R$_1$' is hydrogen or benzyl, and wherein the benzyl is optionally substituted,
or its tautomers, isomers, analogs, derivatives or salts thereof.
said method comprising steps of:
c) reacting amino alcohol with an aldehyde in presence of a base to obtain the compound of Formula I wherein 'R$_1$' is hydrogen, 'R' is selected from a group consisting of indole, imidazole, phenyl, chromene-4-one and dihydrobenzofuran, and said 'R' is optionally substituted; and
d) optionally, reacting the compound of Formula I of step (a) with a substituted benzyl halide to obtain the compound of Formula I, wherein 'R' is phenyl which is optionally substituted, and 'R$_1$' is benzyl which is optionally substituted;

In an embodiment of the present disclosure, the amino alcohol of the aforesaid process is 1-(2-amino)-1-(4-methoxy-phenyl-ethyl)-cyclohexanol; the substituted benzyl halide is 4-(2-cyanophenyl)benzyl bromide; the base is selected from a group comprising potassium carbonate, sodium carbonate and a combination thereof; and the aldehyde is selected from a group comprising

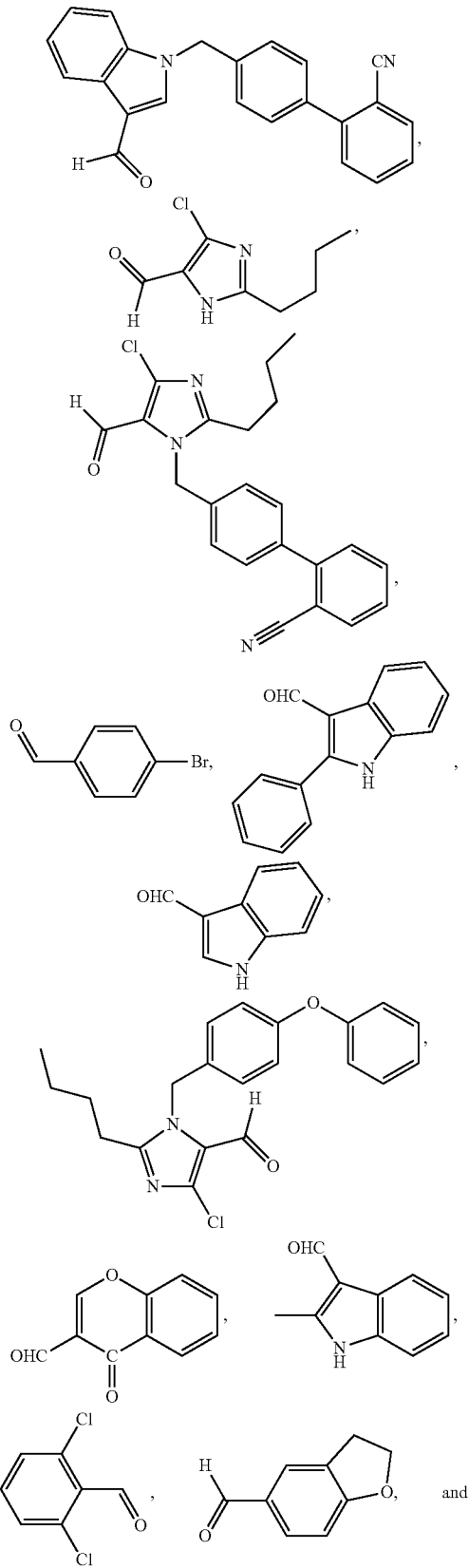

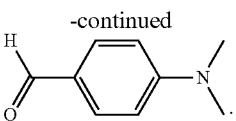

In yet another embodiment of the present disclosure, the process described above is carried out in a solvent selected from a group comprising methanol, ethanol, DMSO, DMF, Ethyl acetate, Ether and combinations thereof.

In still another embodiment of the present disclosure, the process described above is carried out at temperature ranging from about 25° C. to about 30° C.; and for time period ranging from about 4 hours to about 5 hours.

In still another embodiment of the process described above, the compound of Formula I is extracted, dried and re-crystallized.

The present disclosure further relates to a method of inhibiting a protein selected from a group comprising tyrosine kinase, Signal Transducer and Activator of Transcription (STAT) and a combination thereof in a cancer cell, said method comprising act of contacting the compound of claim 1 with the cancer cell for inhibiting the protein.

In an embodiment of the method described above, the tyrosine kinase is selected from a group comprising Janus kinase 1 (JAK1), Janus kinase 2 (JAK2), c-Src kinase and combinations thereof; and the STAT is Signal Transducer and Activator of Transcription 3 (STAT3).

In yet another embodiment of the method described above, concentration of the compound of Formula I ranges from about 7.3 µM to about 50 µM.

In still another embodiment of the method described above, the inhibition of the tyrosine kinase leads to inhibition of STAT3 activation.

In still another embodiment of the method described above, the inhibition of STAT3 activation is carried out by suppressing STAT3 phosphorylation at tyrosine 705 (Y705) residue.

In still another embodiment of the method described above, the phosphorylation is selected from a group comprising constitutive phosphorylation, interleukin-6 (IL-6) induced phosphorylation and a combination thereof; and the constitutive phosphorylation is regulated by tyrosine kinase.

In still another embodiment of the method described above, the inhibition of STAT3 activation result in reduction in nuclear localization of STAT3 in cancer cell.

In still another embodiment of the present disclosure, the method described above inhibits Janus kinase-Signal Transducer and Activator of Transcription (JAK-STAT) pathway in the cancer cell.

In still another embodiment of the present disclosure, the method described above treats cancer, and the cancer is selected from a group comprising hepatocellular carcinoma (HCC), leukemia, lymphoma, prostate cancer, breast cancer, ovarian cancer, multiple myeloma, head and neck cancer, gastric cancer and combinations thereof.

The present disclosure relates to compounds efficient in cancer treatment and corresponding methods thereof. In particular, a compound of Formula I and corresponding synthesis is provided wherein said Formula I compounds are potent modulators of Janus kinase-Signal Transducer and Activator of Transcription (JAK-STAT) pathway in cancer cells, particularly hepatocellular carcinoma (HCC). The Formula I compounds exhibit significantly improved anti-cancer activity by inhibiting/abrogating JAK-STAT3 pathway in carcinoma cells and thereby inducing apoptosis due to the downregulation/inhibition of STAT3 signaling (both in-vitro and in-vivo). Said compounds enhance cytotoxicity of cancer cells, deplete the nuclear pool of STAT3, downregulate constitutively active and inducible upstream kinases, STAT3 and expression of target genes in-vitro and in-vivo.

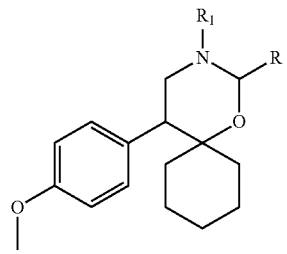

Formula I where, 'R' is selected from a group consisting of indole, imidazole, phenyl, chromene-4-one and dihydrobenzofuran; and wherein said 'R' is optionally substituted;

'R$_1$' is hydrogen or benzyl; and wherein the benzyl is optionally substituted;

or its tautomers, isomers, analogs, derivatives or salts thereof.

In an embodiment of the present disclosure, exemplary compounds of Formula I are provided below (compounds 1-13):

Compound 1

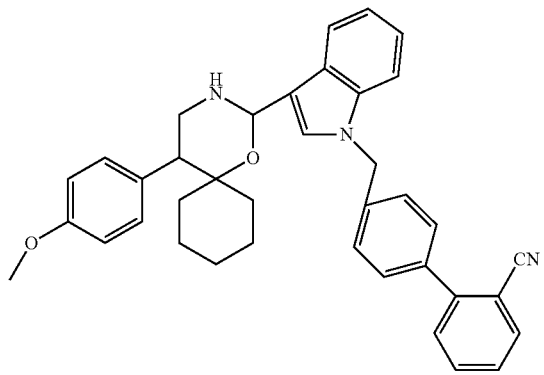

2-(1-(4-(2-cyanophenyl)1-benzyl-1H-indol-3-yl)-5-(4-methoxy-phenyl)-1-oxa-3-aza spiro(5,5) undecane [CIMO]

Compound 2

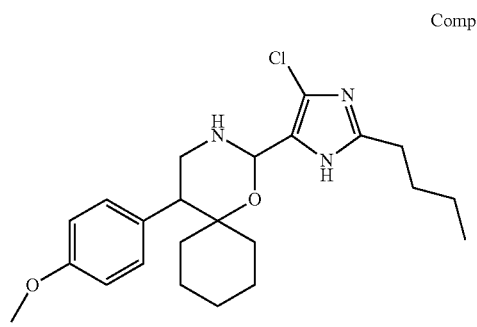

2-(2-butyl-5-chloro-3H-imidazol-4-yl)-5-(4-methoxy-phenyl)-1-oxa-3-aza spiro(5,5) undecane Compound 3

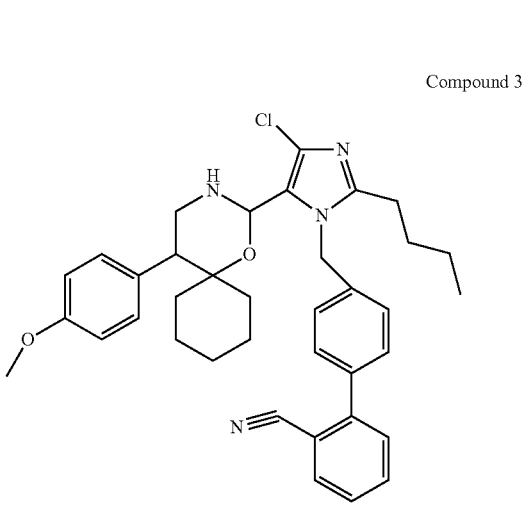 [SMILES: CCCCc1nc(Cl)c(C2NCC(c3ccc(OC)cc3)C3(CCCCC3)O2)n1Cc1ccc(-c2ccccc2C#N)cc1]

2-(2-butyl-5-chloro-3-(4-(2-cyanophenyl)1-benzyl)-imidazol-4-yl)-5-(4-methoxy-phenyl)-1-oxa-3-aza spiro(5,5) undecane Compound 4

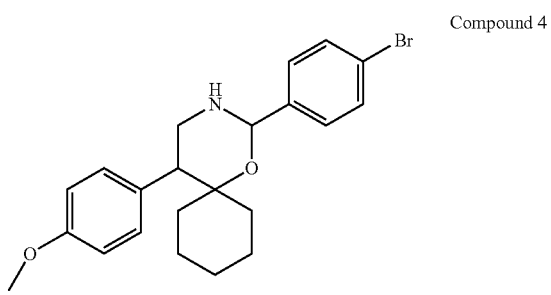 [SMILES: COc1ccc(C2CNC(c3ccc(Br)cc3)OC23CCCCC3)cc1]

2-(4-Bromophenyl)-5-(4-methoxy-phenyl)-1-oxa-3-aza spiro(5,5) undecane

Compound 5

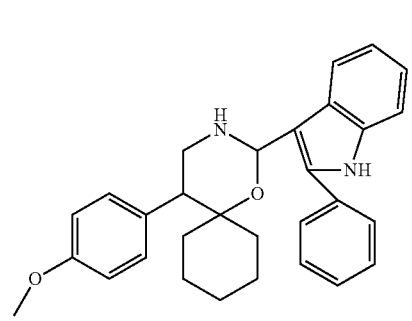

11

2-(2-phenyl indyl)-5-(4-methoxy-phenyl)-1-oxa-3-aza spiro(5,5) undecane

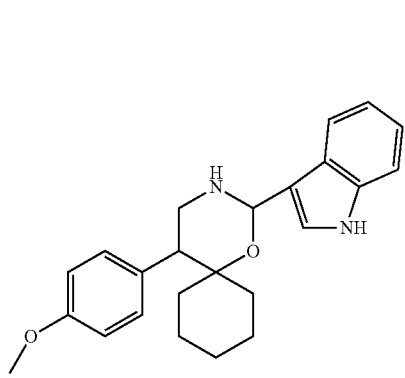

2-(indyl)-5-(4-methoxy-phenyl)-1-oxa-3-aza spiro(5,5) undecane

Compound 6

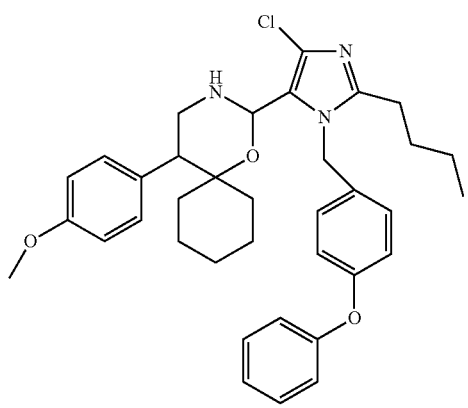

2-(2-butyl-5-chloro-3-(4-benzyloxy-1-benzyl)-imidazol-4-yl)-5-(4-methoxy-phenyl)-1-oxa-3-aza spiro (5, 5) undecane Compound 7

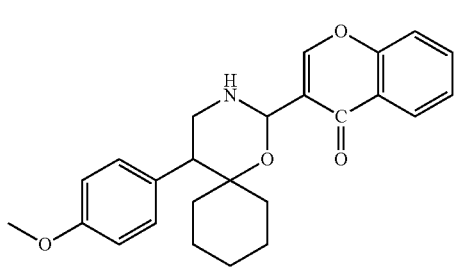

Compound 8

12

3-[5-(4-Methoxy-phenyl)-1-oxa-3-aza-spiro[5.5]undec-2-yl]-chromen-4-one

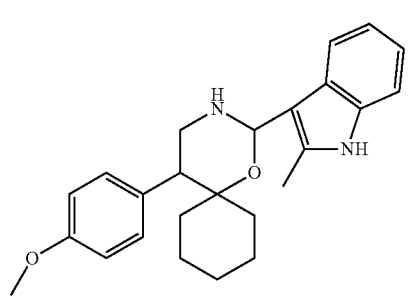

Compound 9

2-(2-methyl indyl)-5-(4-methoxy-phenyl)-1-oxa-3-aza spiro(5,5) undecane

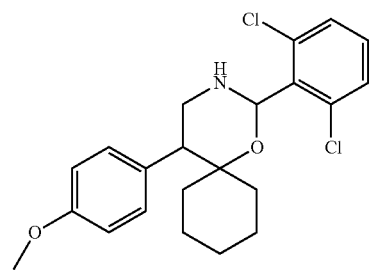

Compound 10

2-(2,6-dichlorophenyl)-5-(4-methoxy-phenyl)-1-oxa-3-aza spiro(5,5) undecane

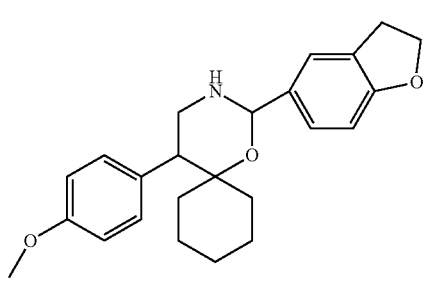

Compound 11

2-(2,3-Dihydro-benzofuran-5-yl)-5-(4-methoxy-phenyl)-1-oxa-3-aza-spiro[5.5]undecane

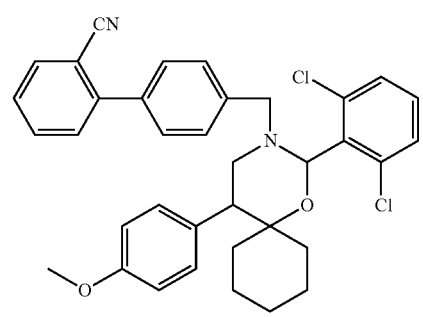

Compound 12

2-(2,6-dichlorophenyl)-5-(4-methoxy-phenyl)-1-oxa-3-(4-(2-cyanophenyl)benzyl azaspiro(5,5) undecane

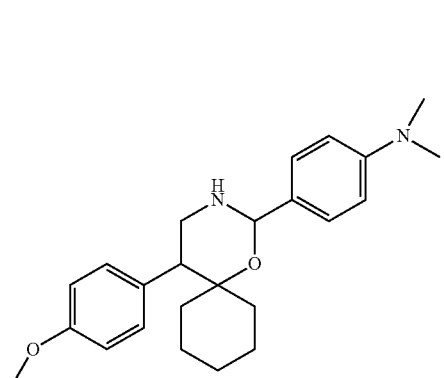

Compound 13

2-(4-dimethyl amino phenyl)-5-(4-methoxy-phenyl)-1-oxa-3-aza spiro(5,5) undecane In an embodiment of the present disclosure, the compounds of Formula I are prepared as per the scheme given below:

SCHEME 1: Synthesis of Formula I (Compounds 1-11 and 13)

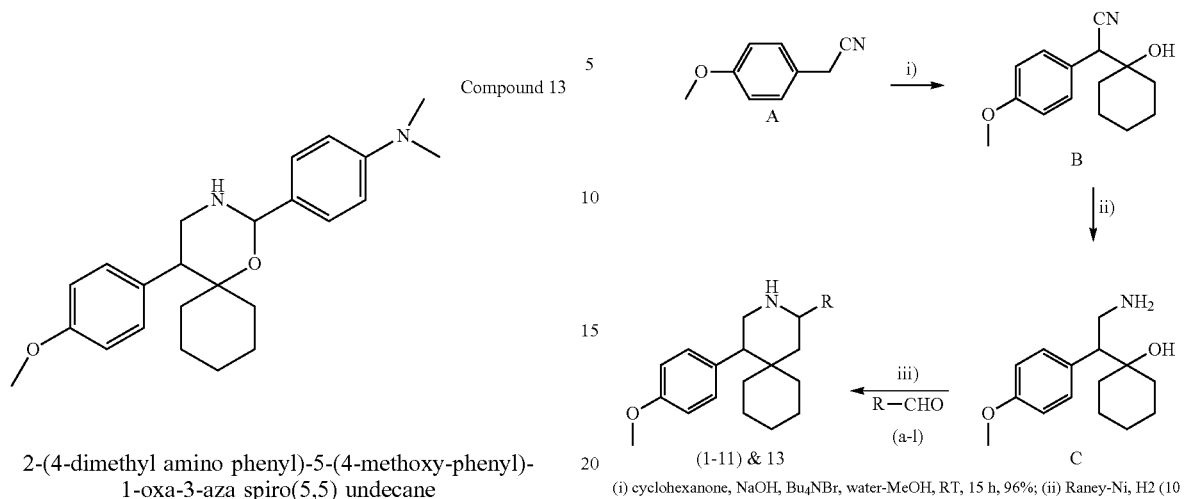

(i) cyclohexanone, NaOH, Bu₄NBr, water-MeOH, RT, 15 h, 96%; (ii) Raney-Ni, H2 (10 atm), anhydrous NH3, MeOH, 35-40° C., 3 h. (iii) R—CHO (a-l), anydrous K₂CO₃/CH₃OH, RT, 4-5 h. [The aldehydes a-1, are recited in Example 1 of the present disclosure]

SCHEME 2: Synthesis of Formula I (Compound 12)

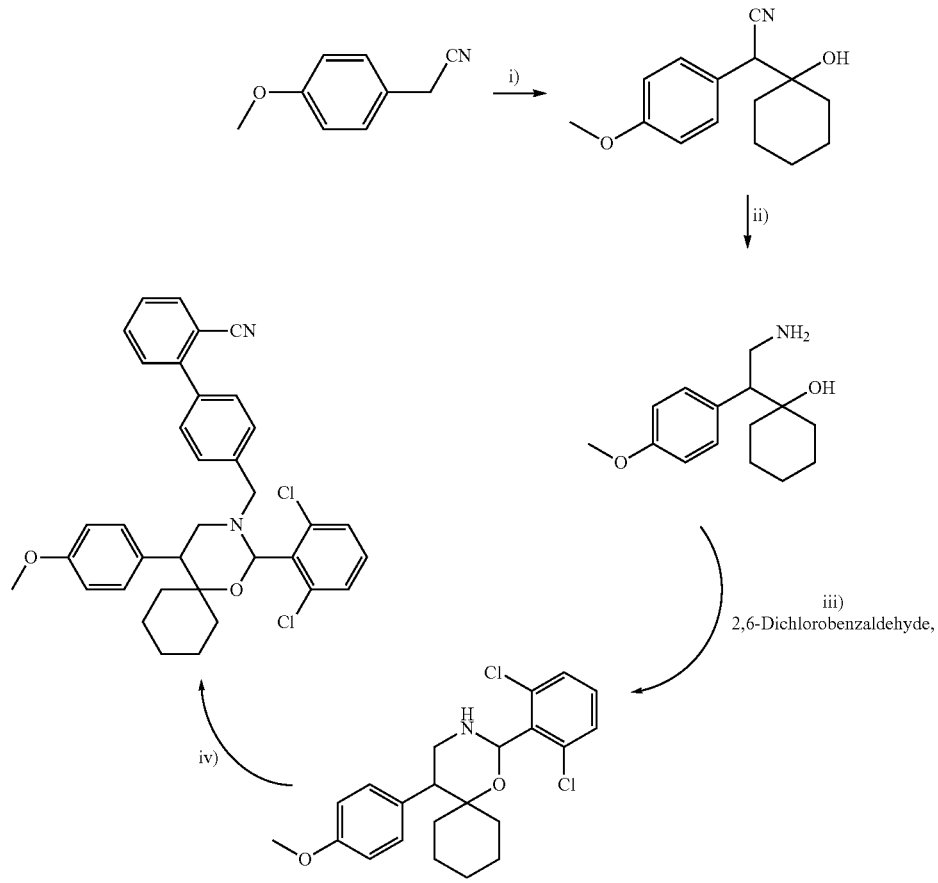

i) cyclohexanone, NaOH, Bu₄NBr, water-MeOH, RT, 15 h, 96%; (ii) Raney-Ni, H2 (10 atm), anhydrous NH3, MeOH, 35-40° C., 3 h.
(iii) 2,6-dichlorobenzaldehyde, anhydrous K₂CO₃/CH₃OH, RT, 4-5 h, (iv) 4-(2-cyanophenyl)benzyl bromide, K₂CO₃/CH₃OH, RT, 10 h The synthetic procedure to prepare Formula I involves adding aldehydes R—CHO [4(a-1)] (about 1.2 eq) and anhydrous potassium carbonate (about 2.5 eq) to a stirred solution of 1-(2-amino)-1-(4-methoxy-phenyl-ethyl)-cyclohexanol (about 1 eq) [Compound C] in methanol (about 10 ml). The reaction mixture is stirred at room temperature (about 25° C. to about 30° C.) for about 4-5 hours. After the completion of the reaction, methanol was evaporated then water is added and the compounds are extracted with ethyl acetate (about 15 ml). The combined organic layer is dried over anhydrous sodium sulphate. The crude solid is obtained on evaporation of the solvent under reduced pressure and recrystallised from hexane and ethyl acetate to furnish crystalline solid viz. Compounds of Formula I.

In an embodiment as described above, Formula I compounds are synthesized by utilizing the multi-component reaction involving 1-[2-amino-1-(4-methoxy-phenyl)-ethyl]-cyclohexanolmonoacetate [Compound A], aryl/benzyl/hetaryl halides, and various aldehydes via. single step condensation and nucleophilic substitution reactions in one step (scheme 1). The Formula I compounds are obtained and recrystallised from hexane and ethyl acetate to furnish crystalline solids. The structures of Formula I compounds are deduced based on IR, $^1$H NMR, $^{13}$C NMR, and LCMS spectroscopic analysis.

In another embodiment of the present disclosure, the compounds of Formula I are potent inhibitors of JAK-STAT pathway and treat cancers/tumors associated with constitutive activation of STAT3 protein. In an exemplary embodiment, the compounds of the present disclosure treat solid and haematological tumors, including not limiting to hepatocellular carcinoma (HCC), leukemia, lymphoma, prostate cancer, breast cancer, head & neck cancer, gastric cancer, ovarian cancer and multiple myeloma.

In another embodiment, the Formula I compounds disrupt STAT3 signaling and have cytotoxic effect on cancer cells. STAT3 is an inducible monomeric transcription factor which dimerizes upon phosphorylation at Y705 and translocates to nucleus. It relay the oncogenic signals by permitting the expression of the target genes involved in uncontrolled cell proliferation, angiogenesis, apoptotic resistance and tumor evasion. Formula I compounds of the present disclosure inhibit constitutive and Interleukin-6 (IL-6) induced activation of STAT3, and the inhibitory effect is specific to tyrosine 705 (Y705) site of STAT3 in cancer cells. In other words, Formula I compounds specifically inhibit Y705 phosphorylation in STAT3 while showing no effect on S727 phosphorylation in cancer cells. The inhibitory effect of Formula I compounds on STAT3 phosphorylation is further evident from the downregulation of JAK1, JAK2, and c-Src proteins (JAK and c-Src proteins are the foremost tyrosine kinases with critical role in STAT3 phosphorylation). These results confirm the Formula I compound mediated blockade of upstream protein tyrosine kinases (JAK and c-Src proteins) in regulating aberrant behavior of STAT3 in the cancer cells.

Restriction of nuclear translocation and accumulation of STAT3 in the cytoplasm is a hallmark of abrogation of the JAK-STAT pathway. In an embodiment, the compounds of Formula I show reduction in nuclear localization of STAT3 which is directly correlated with the decreased phosphorylation of STAT3. The compounds of the present disclosure downregulate STAT3 regulated tumorigenic proteins including Bcl-2, Bcl-xL, cyclin D1, survivin, ICAM-1 and bid which establishes the role of said compounds in limiting the expression of Inhibitor of apoptosis (IAP) and cell cycle regulating proteins. In addition, PARP and Caspase activated DNAse (CAD) are two well-known substrates of caspase-3 wherein activated caspase-3 catalyzes activation of CAD and cleavage of PARP which results in formation of DNA oligomers. The results of the present disclosure towards cleavage of procaspase-3, PARP and deposition of hypodiploid cells in sub-G1 phase prove the apoptosis inducing effect of Formula I compounds in cancer cells.

In another embodiment, the compounds of the present disclosure demonstrate substantial decline in HCC development in an orthotopic mouse model. This observation is supported by immunohistochemistry analysis data in which Ki-67 (biomarker of proliferation) and phospho-STAT3 levels are significantly downregulated with simultaneous increase in cleaved caspase-3 (biomarker of apoptosis) in tumor tissues treated with Formula I compounds. Thus, these results overall demonstrate the significantly improved efficiency of Formula I as potent antiproliferative agents, which show their effect on cancer in vitro and in vivo via. abrogation of the JAK-STAT signaling cascade particularly due to inhibition/downregulation of JAK1, JAK2, and c-Src proteins and the subsequent inhibition of STAT3 phosphorylation at Y705.

The present disclosure also relates to pharmaceutical compositions comprising one or more compounds of Formula I, optionally along with pharmaceutically acceptable excipients. In an embodiment, the pharmaceutically acceptable excipient is selected from a group comprising adjuvant, diluent, carrier, granulating agents, binding agents, lubricating agents, disintegrating agent, sweetening agents, glidant, anti-adherent, anti-static agent, surfactant, anti-oxidant, gum, coating agent, coloring agent, flavouring agent, coating agent, plasticizer, preservative, suspending agent, emulsifying agent, plant cellulosic material, spheronization agent, other conventionally known pharmaceutically acceptable excipient or any combination of excipients thereof. In another embodiment, the pharmaceutical composition of the present disclosure is administered through modes selected from a group comprising intraperitoneal administration, hepatoportal administration, intravenous administration, intra articular administration, pancreatic duodenal artery administration and intramuscular administration, or any combination thereof.

As used in the present disclosure, the term "downregulation" refers to the cellular decrease in the quantity of a component, such as protein, in response to an external stimulus/variable. Further, the term "upregulation" refers to an increase of said cellular component in response to an external stimulus/variable.

Additional embodiments and features of the present disclosure will be apparent to one of ordinary skill in art based upon description provided herein. The present disclosure is further elaborated with the following Examples and Figures. However, the Examples and the Figures should not be construed to limit the scope of the present disclosure.

Materials Employed to Arrive at the Examples of the Present Disclosure

Reagents—

Hoechst 33342, MTT, Tris, glycine, NaCl, SDS, and BSA were purchased from Sigma-Aldrich (St. Louis, Mo., USA). DMEM, FBS, and antibiotic-antimycotic mixture were obtained from Invitrogen (Carlsbad, Calif., USA). Rabbit polyclonal antibodies to STAT3 and mouse monoclonal antibodies against phospho-STAT3 (Tyr 705) and Bcl-2, Bcl-xL, cyclin D1, survivin, Bak, Bid, PTP1B, SHPTP1, SHPTP2, pro-caspase-3 and PARP were obtained from Santa Cruz Biotechnology (Santa Cruz, Calif., USA). Antibodies to phospho-specific Src (Tyr 416), Src, phospho-specific JAK1 (Tyr 1022/1023), JAK1, phospho-specific JAK2 (Tyr 1007/1008) and JAK2 were purchased from Cell Signalling Technology (Beverly, Mass., USA). Goat anti-rabbit-HRP conjugate and goat anti-mouse HRP were purchased from Sigma-Aldrich. Nuclear extraction and DNA binding kits were obtained from Active Motif (Carlsbad, Calif., USA). Bacteria-derived recombinant human IL-6 was purchased from ProSpec-TanyTechnoGene Ltd. (Rehovot, Israel).

Cell Lines—

Human hepatocellular carcinoma (HCC) cell lines HepG2 and PLC/PRF5 cells were obtained from American Type Culture Collection (Manassass, Va.). Huh7-Luc, Hep3B and LO2 cells were a gift provided by Prof Kam Man Hui, National Cancer Centre, Singapore. All the cells were cultured in Dulbecco's Modified Eagle Medium (DMEM) containing 1× antibiotic-antimycotic solution with 10% FBS.

In-Vivo Experiments—

All animal experiments were performed according to protocols approved by the SingHealth Institutional Animal Use and Care Committee. For drug efficacy study, eight week-old athymic nu/nu female mice (from Biolasco, Taiwan) were implanted with the Huh 7-Luc cells orthotopically as described in the below examples. When the bioluminescence signal reached $10^6$, mice were treated either with vehicle (1% DMSO), 2 mg/kg of CIMO or 10 mg/kg of CIMO five days a week intraperitoneally. Tumor development was monitored twice a week by measuring the bioluminescence signals. Mice were euthanized when the humane end-point criteria is met by $CO_2$ inhalation. Primary liver tumor and lung tissues were excised, snap-frozen and stored at −80° C. until further analysis.

The biological material mentioned above for carrying out in-vitro and in-vivo biological experiments in the instant invention is not sourced or procured from India, and all the biological experiments (in-vitro and in-vivo) of the instant invention are carried out in Singapore [Cancer Science Institute of Singapore, National University of Singapore (NUS)]. Further, the synthetic experiments (synthesis of compounds of Formula I) are performed in India (Bangalore University, Bangalore).

Example 1

Synthesis and Characterization of Formula I Compounds

Synthesis of 1-(2-amino)-1-(4-methoxyphenylethyl) cyclohexanol [Compound C]

The compound 1-[2-amino-1-(4-methoxy-phenyl)-ethyl]-cyclohexanolmonoacetateis prepared by the condensation reaction of 4-methoxyphenyl acetonitrile with cyclohexanone followed by catalytic hydrogenation which is further followed by reaction with glacial acetic acid.

(I) Synthesis of 2-(1-(4-(2-cyanophenyl)1-benzyl-1H-indol-3-yl)-5-(4-methoxy-phenyl)-1-oxa-3-aza spiro(5,5) undecane [Compound 1] (CIMO)

Compound 1 is obtained in two steps—
(a) Preparation of 2-(1 cyanophenyl)1-benzyl-1H-indole-3-carbaldehyde (a): This compound is obtained by using indole-3-carbaldehyde (1 mmol), 4-(2-cyanophenyl)benzyl bromide (1.2 mmol), potassium carbonate (2.5 mmol), and DMF (8 ml) as solvent and stirring for about 14 hours at RT.

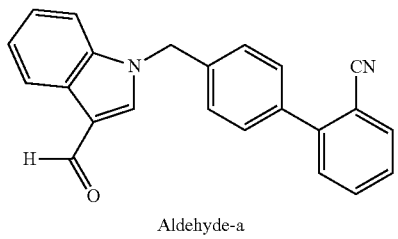 [SMILES: N#Cc1ccccc1-c1ccc(Cn2cc(C=O)c3ccccc32)cc1]

Aldehyde-a (b) Preparation of 2-(1-(4-(2-cyanophenyl)1-benzyl-1H-indol-3-yl)-5-(4-methoxy-phenyl)-1-oxa-3-aza spiro(5, 5) undecane [Compound 1]: This compound is obtained from amino alcohol [compound C] (1 mmol), 2-(1-(4-(2-cyanophenyl)1-benzyl-1H-indole-3-carbaldehyde a, (1 mmol) and potassium carbonate (2.5 mmol) as a brown crystalline solid (yield 89%).

Characterization of Compound 1:
Melting point: 69-70° C.
IR vmax (KBR, $cm^{-1}$): 3270, 2910, 1150.
$^1$H NMR (DMSO, 400 MHz) δ:8.33 (s, 1H, Indole C—H), 8.1 (d, 1H, J=8, aromatic-H), 7.98 (d, 1H, J=8.4, aromatic C—H), 7.80 (d, 1H, J=8.0, aromatic-H) 7.6 (m, 4H, J=8.2, aromatic C—H(biphenyl)), 7.2 (m, 4H, aromatic C—H), 7.4 (d, 1H, J=8.0, aromatic C—H), 6.7-6.9 (dd, J=8.4, aromatic C—H(biphenyl)) 5.57 (s, 1H, O—CH), 4.27 (s, 1H, N—H), 3.85 (s, 1H, $CH_2$—CH), 3.80 (s, 3H, O—$CH_3$) 3.73 (d, 2H, CH—$CH_2$), 3.5 (s, 2H, J=1.6, benzyl-H), 1.0-1.6 (m, 10H, cyclohexyl).
$^{13}$CNMRδ; 157.65, 155.27, 144.04, 138.23, 136.99, 136.81, 133.87, 133.78, 133.66, 133.46, 132.82, 130.55, 130.44, 130.03, 128.95, 128.19, 127.33, 125.51, 122.67, 121.66, 120.75, 118.45, 114.08, 113.17, 112.87, 110.51, 110.10, 72.20, 72.03, 62.11, 54.85, 54.77, 48.78, 36.90, 34.13, 33.53, 25.56, 21.61, 21.34.
Anal. Calcd. for $C_{38}H_{37}N_3O_2$: C, 80.39; H, 6.57; N, 7.40. found C, 80.25; H, 6.51; N, 7.34%.
MASS; m/z found for $C_{38}H_{37}N_3O_2$ 568.4 ([M+1]$^+$).

(II) Synthesis of 2-(2-butyl-5-chloro-3H-imidazol-4-yl)-5-(4-methoxy-phenyl)-1-oxa-3-aza spiro(5,5) undecane [Compound 2]

Compound 2 is obtained from amino alcohol [compound C] (1 mmol), 2-butyl-5-chloro-4,5-dihydro-3H-imidazolylaldehyde b, (1 mmol) and potassium carbonate (2.5 mmol) as reddish brown crystalline solid (yield 88%).

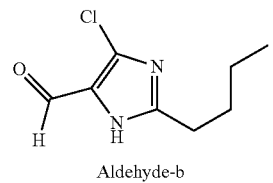

Aldehyde-b

Characterization of Compound 2:
Melting point: 108-110° C.
IR vmax (KBR, $cm^{-1}$): 3340, 2895, 1050
$^1$H NMR ($CDCl_3$, 400 MHz) δ:7.85 (s, 1H, Imido NH), 7.25 (d, 2H, Ar—H), 6.82 (d, 2H, Ar—H), 4.9 (s, 1H, —O—CH), 4.2 (s, 1H, —NH—), 3.9 (t, 1H, $CH_2$—CH), 2.9 (d, 2H, —CH—$CH_2$—), 2.6 (t, 2H, —$CH_2$—$CH_2$) 0.8-1.85 (m, 14H, cyclohexyl, alkyl), 0.9 (t, 3H, $CH_2$—$CH_3$).

(III) Synthesis of 2-(2-butyl-5-chloro-3-(4-(2-cyanophenyl)1-benzyl)-imidazol-4-yl)-5-(4-methoxy-phenyl)-1-oxa-3-aza spiro(5,5) undecane [Compound 3]

Compound 3 is obtained in two steps:

(a) Preparation of 2-(2-butyl-5-chloro-3-(4-(2-cyanophenyl)1-benzyl)-imidazol aldehyde (c): This aldehyde is obtained by using 2-butyl-5-chloro-4,5-dihydro-3H-imidazolylaldehyde (1 mmol), 4-(2-cyanophenyl)benzyl bromide (1.2 mmol), potassium carbonate (2.5 mmol), and DMF (8 ml) as solvent and stirring for about 14 hours at RT.

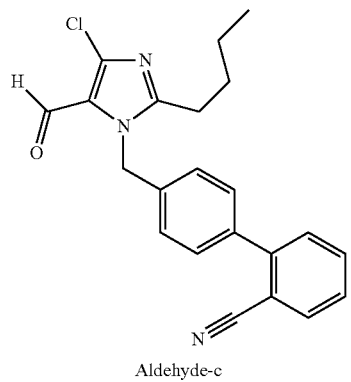 [SMILES: CCCCc1nc(Cl)c(C=O)n1Cc1ccc(-c2ccccc2C#N)cc1]

Aldehyde-c (b) Preparation of 2-(2-butyl-5-chloro-3-(4-(2-cyanophenyl)1-benzyl)-imidazol-4-yl)-5-(4-methoxy-phenyl)-1-oxa-3-aza spiro(5,5) undecane [Compound 3]: This compound is obtained from amino alcohol [Compound C] (1 mmol), 2-(2-butyl-5-chloro-3-(4-(2-cyanophenyl)1-benzyl)-imidazol aldehyde (c), (1 mmol) and potassium carbonate (2.5 mmol) as brown color crystalline solid (yield 89%).

Characterization of Compound 3:

Melting point: 59-60° C.

IR vmax (KBR, cm$^{-1}$): 3265, 2914, 1170.

$^1$H NMR (DMSO, 400 MHz) δ: 7.3-7.7 (m, 6H, aromatic-H), 6.69-7.02 (m, 6H, aromatic-H), 5.29 (s, 1H, methyne), 5.10 (2H, s, benzyl), 3.75 (3H, s, O—CH$_3$), 3.35 (1H, t, methyne), 3.1 (1H, s, N—H), 2.9 (2H, d, CH$_2$), 2.50 (t, 2H, CH$_2$), 1.0-1.7 (m, 17H, cyclohexyl, butyl).

Anal. Calcd. for $C_{37}H_{41}N_4ClO_2$: C, 72.95; H, 6.78; N, 9.20. found C, 72.75; H, 6.51; N, 9.14%.

MASS; m/z found for $C_{37}H_{41}N_4ClO_2$ 610.2 ([M+1]$^+$)

(IV) Synthesis of 2-(4-Bromophenyl)-5-(4-methoxy-phenyl)-1-oxa-3-aza spiro(5,5) undecane [Compound 4]

Compound 4 is obtained from amino alcohol [Compound C] (1 mmol), 4-Bromo benzaldehyde d (1 mmol) and potassium carbonate (2.5 mmol) as colorless crystalline solid (yield 90%).

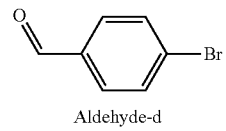

Aldehyde-d

Characterization of Compound 4:

Melting point: 79-80° C.

IR vmax (KBR, cm$^{-1}$): 3290, 2910, 1210.

$^1$H NMR (CDCl$_3$, 400 MHz) δ:7.40-7.45 (m, 4H, aromatic C—H), 7.06 (d, 1H, J=8.4, aromatic C—H), 7.02 (d, 1H, J=8, aromatic C—H), 6.78 (d, 1H, J=8.8, aromatic C—H), 6.73 (d, 1H, J=8.8, aromatic C—H), 5.34 (s, 1H, O—CH), 4.0 (s, 1H, N—H), 3.73 (s, 3H, OCH$_3$), 3.50 (t, 1H, CH$_2$—CH), 3.01 (d, 2H, CH—CH$_2$), 0.8-1.8 (m, 10H, cyclohexyl).

Anal. Calcd. for $C_{22}H_{26}BrNO_2$: C, 63.46; H, 6.29; N, 3.36. found C, 63.34; H, 6.41; N, 3.25%.

MASS; m/z found for $C_{22}H_{26}BrNO_2$ 416.1, 418.1 ([M+1]$^+$).

(V) Synthesis of 2-(2-phenyl indyl)-5-(4-methoxy-phenyl)-1-oxa-3-aza spiro(5,5) undecane [Compound 5]

Compound 5 is obtained from amino alcohol (Compound C) (1 mmol), 2-phenyl indole-3-carbaldehyde e, (1 mmol) and potassium carbonate (2.5 mmol) as colorless crystalline solid (yield 90%).

Aldehyde-e

Characterization of Compound 5:

Melting point: 80-82° C.

IR vmax (KBR, cm$^{-1}$): 3310, 2890, 1170.

$^1$H NMR (DMSO, 400 MHz) δ:11.67 (s, 1H, Indole N—H), 8.12 (d, 2H, J=7.6, aromatic-H), 7.49-7.30 (m, 3H, aromatic C—H) 6.8 (d, 2H, J=8.2, aromatic C—H), 7.05-7.07 (m, 2H, aromatic C—H), 7.13-7.19) (m, 4H, aromatic C—H), 4.44 (s, 1H, O—CH), 4.29 (dd, 1H, J=3.2 CH$_2$—CH), 3.71 (s, 3H, O—CH$_3$), 3.66 (dd, 1H, CH$_2$—CH) 3.29 (s, 1H, N—H), 2.5 (t, 1H, J=1.6, CH$_2$—CH), 1.0-1.6 (m, 10H, cyclohexyl).

Anal. Calcd. for $C_{30}H_{32}N_2O_2$: C, 79.61; H, 7.13; N, 6.19. found C, 79.65; H, 7.01; N, 6.14%.

MASS; m/z found for $C_{30}H_{32}N_2O_2$ 453.3 ([M+1]$^+$).

(VI) Synthesis of 2-(indyl)-5-(4-methoxy-phenyl)-1-oxa-3-aza spiro(5,5) undecane [Compound 6]

Compound 6 is obtained from amino alcohol [Compound C] (1 mmol), indole-3-carbaldehyde f (1 mmol) and potassium carbonate (2.5 mmol) as brown crystalline solid (yield 93%).

Aldehyde-f

Characterization of Compound 6:
Melting point: 112-113° C.
IR vmax (KBR, cm$^{-1}$): 3260, 2910, 1150.
$^1$H NMR (DMSO, 400 MHz) δ:11.5 (s, 1H, Indole N—H), 8.05 (d, 1H, J=7.6, aromatic C—H) 7.08-7.20 (m, 4H, aromatic C—H), 7.7 (s, 1H, aromatic C—H), 6.8 (d, 2H, J=8.0, aromatic C—H), 7.45 (d, 1H, J=8, aromatic C—H), 4.9 (s, 1H, O—CH), 4.22 (s, 1H, N—H), 3.85 (d, 2H, CH$_2$—CH), 3.75 (s, 3H$_2$O—CH$_3$), 3.0 (t, 1H, J=6.5, CH—CH$_2$), 1.0-1.8 (m, 10H, cyclohexyl).
$^{13}$CNMRδ; 157.56, 136.92, 133.67, 130.93, 130.41, 130.00, 124.79, 122.32, 121.29, 120.29, 114.29, 113.25, 112.85, 111.71, 72.28, 72.07, 62.15, 55.87, 54.75, 41.58, 36.92, 34.10, 25.58, 21.33, 21.20.
Anal. Calcd. for C$_{24}$H$_{28}$N$_2$O$_2$: C, 76.56; H, 7.50; N, 7.44. found C, 76.65; H, 7.51; N, 7.23%.
MASS; m/z found for C$_{24}$H$_{28}$N$_2$O$_2$ 377.4 ([M+1]$^+$).

(VII) Synthesis of [Compound 7]

Compound 7 is obtained in two steps—
(a) Preparation of 2-(2-butyl-5-chloro-3-(4-benzyloxyl-benzyl)-imidazol aldehyde (g): This compound is obtained by using 2-butyl-5-chloro-4,5-dihydro-3H-imidazolylaldehyde (1 mmol), 1-(bromomethyl)-4-phenoxybenzene (1.2 mmol), potassium carbonate (2.5 mmol), and DMF (8 ml) as a solvent and stirring for about 14 hours at RT.

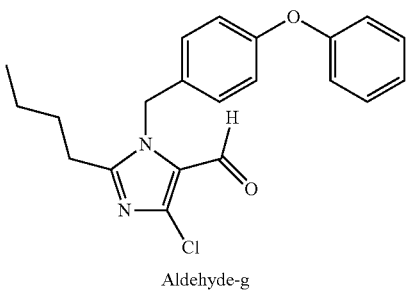 [SMILES: CCCCc1nc(Cl)c(C=O)n1Cc1ccc(Oc2ccccc2)cc1]

Aldehyde-g (b) Preparation of 2-(2-butyl-5-chloro-3-(4-(2-cyanophenyl)1-benzyl)-imidazol-4-yl)-5-(4-methoxy-phenyl)-1-oxa-3-aza spiro(5,5) undecane [Compound 7]: This compound was obtained from amino alcohol [Compound C] (1 mmol), 2-(2-butyl-5-chloro-3-(4-benzyloxyl-benzyl)-imidazol aldehyde g, (1 mmol) and potassium carbonate (2.5 mmol) as brown color crystalline solid (yield 89%).
Characterization of Compound 7:
Melting point: 55-57° C.
IR vmax (KBR, cm$^{-1}$): 3290, 2920, 1150.
$^1$H NMR (DMSO, 400 MHz) δ: 6.6-7.3 (m, 13H, aromatic-H), 5.39 (s, 1H, methyne), 5.29 (2H, s, benzyl), 3.76 (3H, s, O—CH$_3$), 3.37 (1H, t, methyne), 3.2 (1H, s, N—H), 2.60 (2H, t, CH$_2$), 2.56 (d, 2H, CH$_2$), 0.9-1.7 (m, 17H, cyclohexyl, butyl).

Anal. Calcd. for C$_{36}$H$_{42}$N$_3$ClO$_3$: C, 72.05; H, 7.05; N, 7.00. found C, 71.95; H, 6.91; N, 6.94%.
MASS; m/z found for C$_{36}$H$_{42}$N$_3$ClO$_3$ 600.4 ([M+1]$^+$)

(VIII) Synthesis of 3-[5-(4-Methoxy-phenyl)-1-oxa-3-aza-spiro[5.5]undec-2-yl]-chromen-4-one [Compound 8]

Compound 8 is obtained from amino alcohol [Compound C] (1 mmol), 4-oxo-4H-chromene-3-carbaldehyde h (1 mmol) and potassium carbonate (2.5 mmol) as yellow color crystalline solid (yield 85%).

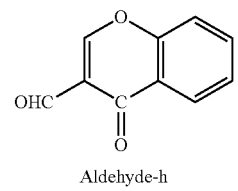 [SMILES: O=Cc1coc2ccccc2c1=O]

Aldehyde-h

Characterization of Compound 8:
Melting point: 59-60° C.
IR vmax (KBR, cm$^{-1}$): 3280, 2945, 1095.
$^1$H NMR (DMSO, 400 MHz) δ:7.66 (s, 1H, aromatic-H (O—CH)), 6.5-7.4 (m, 8H, aromatic-H), 5.5 (s, 1H, O—CH), 4.1 (s, 1H, N—H), 3.75 (s, 3H, O—CH$_3$), 3.5 (t, 1H, CH$_2$—CH) 2.8 (d, 2H, CH—CH$_2$), 0.9-1.7 (m, 10H, cyclohexyl).
$^{13}$C NMRδ; 191, 157.52, 157.30, 156, 133, 132, 131, 130, 129, 124, 123, 118, 117, 113.35, 112.9, 71.9, 71.2, 56.34, 54.32, 40.13, 36.14, 36, 31, 25.39, 21.2, 20.3.
Anal. Calcd. for C$_{25}$H$_{27}$NO$_4$: C, 74.05; H, 6.71; N, 3.45. found C, 73.95; H, 6.51; N, 3.34%.
MASS; m/z found for C$_{25}$H$_{27}$NO$_4$ 406.2 ([M+1]$^+$)

(IX) Synthesis of 2-(2-methyl indyl)-5-(4-methoxy-phenyl)-1-oxa-3-aza spiro(5,5) undecane [Compound 9]

Compound 9 is obtained from amino alcohol [compound C] (1 mmol), 2-methyl indole-3-carbaldehyde i (1 mmol) and potassium carbonate (2.5 mmol) as colorless crystalline solid (yield 85%).

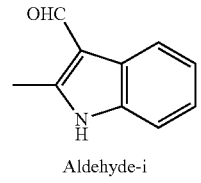

Aldehyde-i

Characterization of Compound 9:
Melting point: 158-160° C.
IR vmax (KBR, cm-1): 3270, 3010, 1165.
1H NMR (DMSO, 400 MHz) δ:11.30 (s, 1H, Indole N—H), 7.9 (d, 1H, J=7.6, aromatic C—H) 7.25 (d, 1H, J=7.6, aromatic C—H), 7.16 (d, 2H, J=8.4, aromatic C—H), 6.9-7.1 (m, 2H, aromatic C—H), 6.78 (d, 2H, J=8.8, aromatic C—H), 4.8 (s, 1H, O—CH), 4.16 (dd, 1H, CH2-CH), 3.7 (dd, 1H, J=4.8, CH2-CH), 3.67 (s, 3H, O—CH3), 2.88 (t, 1H, J=1.6, CH2-CH), 2.41 (s, 3H, methyl), 2.07 (s, 1H, N—H), 1.0-1.6 (m, 10H, cyclohexyl).

Anal. Calcd. for C25H30N2O2: C, 76.89; H, 7.74; N, 7.17. found C, 76.65; H, 7.51; N, 7.14%.
MASS; m/z found for C25H30N2O2 391.2 ([M+1]+).

(X) Synthesis of 2-(2,6-dichlorophenyl)-5-(4-methoxy-phenyl)-1-oxa-3-aza spiro(5,5) undecane [Compound 10]

Compound 10 is obtained from amino alcohol [Compound C] (1 mmol), 2,6-dichloro Benzaldehyde j (1 mmol) and potassium carbonate (2.5 mmol) as brown color crystalline solid (yield 89%).

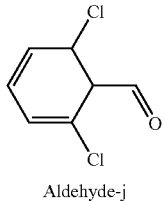

Aldehyde-j

Characterization of Compound 10:
Melting point: 58-60° C.
IR vmax (KBR, cm$^{-1}$): 3250, 2870, 1124.
$^1$H NMR (CDCl$_3$, 400 MHz) δ: 7.40 (m, 3H, J=7, Ar—H), 7.10 (d, 2H, J=8, Ar—H), 6.88 (d, 2H, J=7.6, Ar—H), 5.71 (d, 1H, —NH), 3.81 (s, 3H, OCH$_3$), 3.52 (d, 2H, —CH$_2$—CH—), 3.31 (s, 3H, Ar—CH), 2.45-2.95 (m, 2H, —CH—CH$_2$), 0.95-1.75 (m, 10H, cyclohexyl).
Anal. Calcd. for C$_{22}$H$_{25}$Cl$_2$NO$_2$: C, 65.03; H, 6.20; N, 3.45. found C, 65.05; H, 6.11; N, 3.34%.
MASS; m/z found for C$_{22}$H$_{25}$Cl$_2$NO$_2$ 407.1 ([M+1]$^+$)

(XI) Synthesis of 2-(2,3-Dihydro-benzofuran-5-yl)-5-(4-methoxy-phenyl)-1-oxa-3-aza-spiro[5.5]undecane [Compound 11]

Compound 11 is obtained from amino alcohol 3 (1 mmol), 2,3-dihydrobenzofuran-5-carbaldehyde k (1 mmol) and potassium carbonate (2.5 mmol) as colorless crystalline solid (yield 88%).

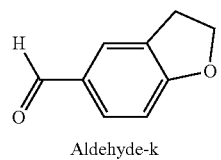 [SMILES: O=Cc1ccc2c(c1)CCO2]

Aldehyde-k

Characterization of Compound 11:
Melting point: 78-80° C.
IR vmax (KBR, cm$^{-1}$): 3275, 2910, 1195.
$^1$H NMR (DMSO, 400 MHz): 7.05 (d, 2H, aromatic-H), 6.5-7.0 (m, 5H, aromatic-H), 5.29 (s, 1H, O—CH), 4.2 (t, 2H, CH$_2$) 4.1 (s, 1H, N—H), 3.8 (s, 3H, O—CH$_3$), 3.4 (t, 1H, CH$_2$—CH), 3.0 (2H, t, CH$_2$) 2.9 (d, 2H, CH—CH$_2$), 0.9-1.7 (m, 10H, cyclohexyl).
Anal. Calcd. for C$_{24}$H$_{29}$NO$_3$: C, 75.96; H, 7.70; N, 3.69. found C, 75.85; H, 7.51; N, 3.54%.
MASS; m/z found for C$_{24}$H$_{29}$NO$_3$ 380.4 ([M+1]$^+$)

(XII) Synthesis of 2-(2,6-dichlorophenyl)-5-(4-methoxy-phenyl)-1-oxa-3-(4-(2-cyanophenyl)benzyl azaspiro(5,5) undecane [Compound 12]

Compound 12 is obtained from 2-(2,6-dichlorophenyl)-5-(4-methoxy-phenyl)-1-oxa-3-aza spiro(5,5) undecane [compound 10] (1 mmol), 4-(2-cyanophenyl)benzyl bromide (1.2 mmol) and potassium carbonate (2.5 mmol) as colorless crystalline solid (yield 87%).
Characterization of Compound 12:
Melting point: 81-83° C.
IR vmax (KBR, cm$^{-1}$): 3295, 2989, 1151.
$^1$H NMR (DMSO, 400 MHz) δ:7.75 (d, 1H, aromatic-H), 7.65 (t, 1H, aromatic-H), 7.2-7.5 (m, 11H, aromatic-H), 7.1 (d, 1H, aromatic-H), 6.75 (1H, t, aromatic-H), 6.1 (s, 1H, O—CH), 4.45 (s, 2H, benzyl-H), 3.7 (d, 2H, N—CH$_2$), 3.5 (t, 1H, CH$_2$—CH), 3.3 (s, 3H, O—CH$_3$), 0.9-1.5 (m, 1 OH, cyclohexyl).
Anal. Calcd. for C$_{36}$H$_{34}$N$_2$Cl$_2$O$_2$: C, 74.05; H, 6.71; N, 3.45. found C, 73.95; H, 6.51; N, 3.34%.
MASS; m/z found for C$_{36}$H$_{34}$N$_2$Cl$_2$O$_2$ 598.6 ([M+1]$^+$)

(XIII) Synthesis of 2-(4-dimethyl amino phenyl)-5-(4-methoxy-phenyl)-1-oxa-3-aza spiro(5,5) undecane [Compound 13]

Compound 13 is obtained from amino alcohol [compound C] (1 mmol), 4-(dimethylamino) benzaldehyde l (1 mmol) and potassium carbonate (2.5 mmol) as brown color crystalline solid (yield 89%).

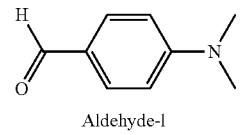

Aldehyde-l

Characterization of Compound 13:
Melting point: 120-121° C.
IR vmax (KBR, cm$^{-1}$): 3280, 2866, 1118.
$^1$H NMR (CDCl$_3$, 400 MHz) δ:7.5 (d, 2H, J=7.2, aromatic C—H), 7.10 (d, 2H, J=8.4, aromatic C—H), 6.7 (d, 2H, J=8, aromatic C—H), 6.6 (d, 2H, J=8.4, aromatic C—H), 5.35 (s, 1H, O—CH), 3.9 (t, 1H, CH$_2$—CH), 3.73 (s, 1H, N—H), 3.69 (s, 3H$_2$O—CH$_3$), 2.90 (s, 6H, N—CH$_3$, N—CH$_3$), 2.8 (t, 2H, CH$_2$—CH) 1.0-1.8 (m, 1 OH, cyclohexyl).
Anal. Calcd. for C$_{24}$H$_{34}$N$_2$O$_2$: C, 75.75; H, 8.48; N, 7.36. found C, 75.65; H, 8.51; N, 7.23%.
MASS; m/z found for C$_{24}$H$_{34}$N$_2$O$_2$ 381.2 ([M+1]$^+$).

While representative compounds and their synthesis have been shown and described in this Example 1, various modifications and substitutions may be made thereto without departing from the spirit and scope of the present disclosure. Accordingly, it is to be understood that the compounds synthesized in Example 1 are representative compounds under Formula I, and a person of average skill in the art can arrive at all other possible compounds under Formula I and corresponding synthesis based on the description/examples of the present disclosure. Arriving at such compounds of the present Formula I is within the scope of present disclosure.

Example 2

Formula I Compounds Suppress Proliferation of Cancer Cells in a Dose- and Time-Dependent Manner The anti-proliferative activity of Formula I compounds are studied on HepG2 cells using MTT assay. Briefly, the cells (2.5×10$^4$/ml) are incubated in triplicate in a 96-well plate in the presence or absence of different concentrations of compounds in a final volume of 0.2 ml up to 72 hours at 37° C. Thereafter, 20 µl MTT solution (5 mg/ml in PBS) is added to each well. After 2 hours of incubation at 37° C., 0.1 ml lysis buffer (20% SDS, 50% dimethyl-formamide) is added; incubation is continued overnight at 37° C.; and the optical density (OD) at 570 nm is measured by Tecan plate reader.

Among the tested compounds, Compound 1 [CIMO] is found to be the most effective with an $IC_{50}$ of 7.3 µM, followed by other compounds which have $IC_{50}$ ranging from about 9.8 µM to >50 µM (Table 1). Additionally, Compound 1 is tested on a panel of six cell lines including Hep3B, PLC/PRF5, AGS (gastric cancer cell line), DU145 (prostate cancer cell line), MDA MB231 (breast cancer cell line) and CAL27 (head and neck cancer cell line) cells. Compound 1 exhibits a substantial decrease of viable cells in all six tested cell lines (Table 2) proving that Compound 1 is useful in combating different types of cancer. Further, Formula I Compounds do not show cytotoxic effect on LO2 cells up to 72 hours at 100 µM, thereby proving that Formula I Compounds do not have cytotoxic effect on this non-diseased/normal cell line (Table 3).

TABLE 1

Novel Azaspiranes inhibitory Formula I compounds activity against HepG2 cells after 72 hours

| Compound | $IC_{50}$ µM |
| --- | --- |
| 2 | 38.7 |
| 3 | 14.3 |
| 4 | 37.1 |
| 5 | 9.8 |
| 6 | 28.5 |
| 1 (CIMO) | 7.3 |
| 7 | 15.8 |
| 8 | 28.8 |
| 9 | >50 |
| 10 | 42.4 |
| 11 | >50 |
| 12 | >50 |
| 13 | >50 |

TABLE 2

Effect of Compound 1 against various cancer cell lines

| Compound | $IC_{50}$ (µM) | | | | | | |
| --- | --- | --- | --- | --- | --- | --- | --- |
| | HepG2 | Hep3B | PLC/PRF5 | AGS | MDA MB231 | DU145 | CAL27 |
| Compound 1 | 7.3 | 46.9 | 38.8 | 36.9 | 24.3 | 38.8 | 27.1 |

TABLE 3

Effect of Formula I compounds against LO2 cells after 72 hours

| Compound | $IC_{50}$ µM |
| --- | --- |
| 2 | NA (not applicable) |
| 4 | NA |
| 6 | NA |
| 1 (CIMO) | NA |
| 7 | NA |
| 8 | NA |

Example 3

Compound 1 (CIMO) Causes Accumulation of HepG2 Cells in Sub-G1 Phase

In late apoptosis, activation of endonucleases leads to fragmentation of genomic DNA into oligomers thereby contributing to a decrease in DNA content, which in turn leads to the buildup of cells in Sub-G1 phase. In order to evaluate the effect of Compound 1 on cell cycle distribution of HepG2 cells, flow cytometric analysis is performed. HepG2 cells are treated with CIMO at different time intervals up to 48 hours. Thereafter, cells are washed, fixed with 70% ethanol, and incubated for about 30 minutes about at 37° C. with 0.1% RNaseA in PBS. Cells are then washed again, resuspended, and stained in PBS containing 25 µg/ml propidium iodide (PI) for about 30 minutes at room temperature. Cell distribution across the cell cycle after PI staining is analyzed with a Beckman Coulter flow cytometer.

Interestingly, CIMO increase the accumulation of the sub-G1 cell population to 18.8%, 38.7%, 71% and 92.1% at 16 hours, 24 hours, 36 hours and 48 hours respectively (FIG. 1).

Example 4

Compound 1 (CIMO) Potently Inhibits Constitutive STAT3 Phosphorylation in HCC Cells CIMO is tested towards the inhibition of constitutive activation of STAT3 in HepG2 cells by Western Blotting via antibodies recognising phospho-STAT3 (Y705). For detection of phospho-proteins, CIMO treated whole-cell extracts are lysed in lysis buffer [20 mM Tris (pH 7.4), 250 mM NaCl, 2 mM Ethylenediaminetetraacetic acid (pH 8.0), 0.1% Triton-X-100, 0.01 mg/ml aprotinin, 0.005 mg/ml leupeptin, 0.4 mM phenylmethanesulfonylfluoride, and 4 mM $NaVO_4$). Lysates are then spun at 14,000 rpm for about 10 minutes to remove insoluble material and resolved on SDS gel. After electrophoresis, the proteins are electrotransferred to a nitrocellulose membrane, blocked with 5% non-fat milk, and probed with various antibodies (1:1000) overnight at about 4° C. The blot is washed, exposed to HRP-conjugated secondary antibodies for about 1 hour, and finally examined by chemiluminescence (ECL; GE Healthcare, Little Chalfont, Buckinghamshire, UK).

As shown in FIGS. 2A and 2C, levels of phospho-STAT3 are found to be substantially downregulated in a dose- and time-dependent manner, with maximum inhibition identified at 20 µM and 6 hours. At the same time, STAT3 protein expression remains unchanged (FIGS. 2A and 2C, bottom). Further, it is shown that exposure to AG490, a well-known inhibitor of JAK2, decreases the phosphorylation of STAT3 in a dose-dependent manner in HepG2 cells with the maximum inhibition at 200 µM for 6 hours (FIG. 2B). Thus, it is evident that CIMO shows significantly improved STAT3 phosphorylation inhibition when compared to known JAK inhibitor such as AG490 wherein, CIMO shows a comparable effect already at a ten-fold lower concentration, and hence much higher potency.

Example 5

Effect of Compound 1 (CIMO) on STAT3 Phosphorylation is Specific for Y705

Given that STAT3 can undergo phosphorylation at Y705 or S727, which are mediated by Janus kinase and Akt respectively, and that phospho-STAT3 (S-727) regulates transcription activation in MAPK pathway as well, the effect of CIMO on phosphorylation of Serine-727 in STAT3 is investigated. Here, it is found that CIMO completely inhibits the phosphorylation of Y705, however that it has no effect on phosphorylation of S727 (FIGS. 2C and 2D), establishing that CIMO inhibits upstream tyrosine kinases (JAK and c-Src proteins).

Example 6

Compound 1 (CIMO) Depletes Nuclear Localization of STAT3 in HCC Cells

Inhibition of phosphorylation of STAT3 at Y705 suppresses nuclear translocation of STAT3 and down-regulates the expression of target genes. Hence, it is evaluated whether CIMO can inhibit nuclear translocation of STAT3.

HepG2 cells are plated in chamber slides in DMEM containing 10% FBS and allowed to adhere for about 24 hours. Following treatment with CIMO for about 6 hours, the cells are fixed with cold acetone for about 10 minutes, washed with PBS and blocked with 5% normal goat serum for about 1 hour. The cells are then incubated with rabbit polyclonal anti-human STAT3 Antibody (dilution, $\frac{1}{100}$). After overnight incubation, the cells are washed and then incubated with goat anti-rabbit IgG-Alexa 594 ($\frac{1}{100}$) for about 1 hour and counterstained for nuclei with Hoechst (50 ng/ml) for about 5 minutes. Stained cells are mounted with mounting medium (Sigma-Aldrich) and analyzed under a fluorescence microscope (DP 70, Olympus, Tokyo, Japan).

FIG. 2E clearly demonstrates that CIMO causes a significant decrease of STAT3 in the nucleus of HepG2 cells. This overall represents conclusive evidence that CIMO inhibits phosphorylation of STAT3, and STAT3 is accumulated in the cytoplasm.

Example 7

Compound 1 (CIMO) Suppresses Constitutive Activation of c-Src, JAK1 and JAK2 in HCC Cells Activation of STAT3 is regulated by soluble tyrosine kinases of c-Src and JAK family proteins. CIMO treatment demonstrates significant inhibition of phosphorylation of c-Src kinases, JAK1 and JAK2 (FIG. 2F) without affecting the levels of c-Src, JAK1 and JAK2 proteins. Therefore, these results clearly confirm that inhibition of STAT3 is due to the inhibition of c-Src and JAK family proteins.

Example 8

Compound 1 (CIMO) Inhibits STAT3 DNA Binding Activity in HCC Cells

It is further investigated whether CIMO modulates STAT3 DNA binding activity in HepG2 cells, since it is known that STAT3 dimer translocates into the nucleus and binds to specific DNA nucleotide sequence to regulate gene expression. DNA binding assay is performed using a STAT3 DNA binding TransAM™ ELISA kit (Active Motif, Carlsbad, Calif., USA). Briefly, nuclear extracts (5 µg) from CIMO-treated cells are incubated in a 96-well plate coated with oligonucleotide containing the STAT3-specific DNA probe. Bound STAT3 is then detected by a specific primary antibody. An HRP-conjugated secondary antibody is subsequently applied to detect the bound primary antibody and provided the basis for colorimetric quantification. The enzymatic product is measured at 450 nm with a microplate reader (Tecan Systems, San Jose, Calif., USA). Specificity of this assay is tested by the addition of wild-type or mutated STAT3 consensus oligonucleotide in the competitive or mutated competitive control wells before the addition of the nuclear extracts.

The results clearly prove that CIMO suppresses the binding of STAT3 to the DNA in a time-dependent manner in HepG2 cells (FIG. 2G).

Example 9

CIMO Inhibits STAT3 Mediated Transcription Activity in HepG2 Cells

Increased STAT3 activity is known to stimulate oncogenicity of hepatocellular carcinoma. Therefore, evaluation of the level of phosphorylated STAT3 (Y705) in HepG2 cells is carried out with siRNA-mediated deletion of STAT3 transcripts and/or exposure to CIMO, using Western Blot analysis. Experiments related to transient-transfection of STAT3 siRNA in HepG2 cells and STAT3 mediated Transcription activity are performed wherein 60-70% confluent of cells in a 6-well plate are transfected using FuGENE6 (Roche Molecular Biochemicals, Indianapolis, USA) transfection reagent. Luciferase assay is performed using Dual Luciferase Assay Kit (Promega Corp, Singapore). Transfections are carried out in triplicate using 1 µg of the appropriate α-2 macroglobulin luciferase reporter plasmid and empty vector per transfection along with 0.2 µg of Renilla expression plasmid as control for transfection efficiency. Luciferase activities are assayed 48 hours after transfection using the dual Luciferase Assay System (Promega Corp, Singapore)

Transient-transfection of STAT3 siRNA in HepG2 cells result in decreased levels of phosho-STAT3 and total STAT3 protein compared to their vector control cells, demonstrated using Western Blot. On the other hand, application of CIMO to HepG2 cells result in decreased phospho-STAT3 levels compared to their control cells exposed with DMSO (FIG. 3A). In contrast, the protein levels of total STAT3 are not significantly altered in HepG2 cells on exposure to CIMO, when compared to their DMSO exposed control.

In addition, assessment of STAT3 mediated transcriptional activity using an α2-macroglobulin (α2-M) promoter in HepG2 cells with either siRNA-mediated depletion of STAT3 expression or on exposure to CIMO is carried out as described above (FIG. 3B). The α2-M reporter construct contains a fragment of the α2-M gene promoter (−215 to +8 bp) to which STAT3 binds and induces transcription of this gene. siRNA-mediated depletion of STAT3 expression in HepG2 cells exhibit decreased α2-M promoter activity when compared to their vector control cells. Similarly, on exposure to the CIMO compound, HepG2 cells exhibit decreased α2-M promoter activity when compared to their control cells exposed with DMSO.

Example 10

Compound 1 (CIMO) Downregulates IL-6 Induced JAK1, JAK2 and STAT3 Phosphorylation in HCC Cells Elevated levels of serum IL-6 is associated with various types of cancers, leading to the overactivation of STAT3. Hep3B are HCC cells which lack constitutively active JAK and STAT3 proteins. CIMO substantially down-regulates the IL-6 induced phosphorylation of JAK1, JAK2 and STAT3 in Hep3B cells (FIG. 3C). These results clearly demonstrate that CIMO modulates both constitutive and inducible activation of proteins of the JAK-STAT pathway.

Example 11

Compound 1 (CIMO) Regulates the Expression of STAT3 Targeted Genes Involved in Cell Proliferation and Survival, and Activates Procaspase-3 and Induces Cleavage of PARP STAT3 activation is known to regulate the expression of pro-apoptotic and anti-apoptotic proteins. Therefore, it is investigated whether CIMO modulates the expression of various STAT3 regulated pro-apoptotic and anti-apoptotic genes. It is also studied whether CIMO activates procaspase-3 and induces cleavage of PARP.

To detect STAT3-regulated proteins and PARP, cells ($2 \times 10^6$/ml) are treated with CIMO for the indicated times as shown in respective FIGS. 3E, 3D and 4A. The cells are then washed and protein is extracted by incubation for about 30 minutes on ice in about 0.05 ml buffer containing 20 mM HEPES, pH 7.4, 2 mM EDTA, 250 mM NaCl, 0.1% NP-40, 2 µg/ml leupeptin, 2 µg/ml aprotinin, 1 mM PMSF, 0.5 µg/ml benzamidine, 1 mM DTT, and 1 mM sodium vanadate. The lysate is centrifuged and the supernatant is collected. Whole-cell extract protein (30 µg) is resolved on SDS-PAGE, electrotransferred onto a nitrocellulose membrane, blotted with antibodies against survivin, Bcl-2, Bcl-xL, cyclin D1, Bak, Bid, ICAM-1, procaspase-3, and PARP and then detected by chemiluminescence (ECL; GE Healthcare, Little Chalfont, Buckinghamshire, UK).

Down-regulation of anti-apoptotic proteins including Bcl-2, Bcl-xL, Survivin, ICAM-1, Bid and cell cycle regulator Cyclin D1 is observed. Further, upregulation of pro-apoptotic protein Bak in a time-dependent manner with maximum activity at 36 hours is observed (FIGS. 3D and 3E). This finding provides evidence that CIMO inhibits survival signalling on multiple levels, hence rendering the cell more prone to apoptosis induction.

Further, it is known that activated caspase-3 cleaves the full length PART" (116-kDa) into 85-kDa and 24-kDA fragments. PARP is involved in the DNA repair mechanism and drives the cell to apoptosis. Thus, it is investigated whether suppression of constitutively active STAT3 by CIMO leads to apoptosis. FIG. 4A conclusively demonstrates the activation of procaspase-3 and subsequent decline of full length PARP with increase in cleaved 85-kDa fragment in a time dependent manner. These results clearly indicate that CIMO induces caspase-3-mediated apoptosis in cancer cells.

Example 12

Tyrosine Phosphatases are Involved in CIMO-Induced Inhibition of STAT3 Activation Protein tyrosine phosphatases have been implicated in STAT3 activation. Any decrease in the activity of protein tyrosine phosphatases result in the increased tyrosine phosphorylation of the target proteins. SHP-1, SHPTP-2, PTP1B are some of the major tyrosine phosphatases known to regulate the phosphorylated/dephosphorylated levels of JAK proteins thereby STAT3 activation. Accordingly, it is analyzed whether CIMO-induced inhibition of STAT3 tyrosine phosphorylation could be due to activation of a protein tyrosine phosphatase (PTPase). Treatment of HepG2 cells with the broad spectrum tyrosine phosphatase inhibitor sodium pervanadate prevents CIMO-induced inhibition of STAT3 activation (FIG. 4B). This suggests that tyrosine phosphatases are involved in CIMO-induced inhibition of STAT3 activation. Based on this, the expression of various tyrosine phosphatases including SHP-1, SHPTP-2, PTP1B upon treating with CIMO for up to 4 hours is also analysed and is found that there is no change in levels of these phosphatases (FIG. 4C). Based on these results, the involvement of some other phosphatases in reversal of the effect of CIMO on STAT3 phosphorylation is confirmed.

Example 13

Compound 1 (CIMO) Suppresses CXCL12-Induced HepG2 Cell Migration and Invasion

STAT3 targeted gene products are known to be involved in cancer cell migration. FIG. 5A interprets the movement of cancer cells in the presence and absence of CIMO and C—X—C motif chemokine 12 (CXCL12) protein. CXCL12 is a chemokine which essentially stimulates the swift migration of cancer cells. An IBIDI culture insert (IBIDI GmbH) is developed with two reservoirs separated by a 500 µm thick wall created by a culture insert in a 35 mm petri dish. 70 µl of HepG2 cells ($5 \times 10^5$ cells/ml) are added into the two reservoirs of the same insert and incubated at about 37° C. After 12 hours, the insert is gently removed by creating a gap of ~500 µm. The cells are treated with about 5 µM CIMO for about 8 hours before being exposed to about 100 ng/mL CXCL12 for about 24 hours. Width of wound is measured at time zero and 24 hours of incubation with and without CIMO in the absence or presence of CXCL12. Graphs are plotted against the percentage of migration or distance the cells moved before and after treatment, normalized to control.

FIG. 5A clearly demonstrates that CIMO limits the HepG2 cell migration by nearly 50%, both in the presence and absence of CXCL12, compared to the respective controls.

In case of the invasion assay, the said assay is performed wherein BD (Biocoat™ Matrigel™) Invasion chamber with 8 µm pores in the light-tight polyethylene terephthalate membrane is taken and is coated with a reconstituted basement membrane gel (BD Biosciences). $2 \times 10^5$ cells are suspended in serum-free DMEM and seeded into the Matrigel Transwell chambers. The cells are incubated with CIMO for about 8 hours. After incubation, the outer surfaces of the Transwell chambers are wiped with cotton swabs, and the invading cells are fixed and stained with crystal violet solution. The invading cells are then counted in five randomly selected areas under microscopic observation.

FIG. 5B demonstrates that more than 50% of HepG2 cells motility is inhibited both in the presence and absence of CXCL12 across polyethylene terephthalate membrane, establishing that CIMO interferes with cell invasion.

Example 14

In-Vivo Study

Compound 1 (CIMO) Suppresses the Growth of Human HCC In Vivo and STAT3 Activation in Tumor Tissues The antitumor potential of CIMO is tested in vivo via. intra-peritoneal administration in an orthotopic model of human HCC using Huh 7-Luc transfected cells. 100 µl containing $3 \times 10^6$ Huh 7-Luc cells are injected subcutaneously in the right flank of Nude mice. When the tumor volume reaches approximately 1 $cm^3$, tumor is harvested, cut into 2 $mm^3$ pieces and then implanted orthotopically into the liver of Nude mice. A midline abdominal incision (of about 3-5 cm) is made to expose the whole liver and the liver capsule is mechanically injured with a needle. A single piece of human HCC tissue (~2 $mm^3$) is filled into the liver tissue (which is visible as a white spot) with forceps and the abdominal wall closed. The skin incisions are closed with wound clips. The development of tumors is monitored by imaging and quantification of the bioluminescence signals using the Xenogen IVIS system (Caliper Life Sciences, CA).

It is found that CIMO at a concentration of 10 mg/kg induces significant inhibition of tumor growth compared with the DMSO treated controls (FIG. 6A). An unpaired t-test with Welch's correction are used for statistical comparisons between groups, wherein $p<0.05$ is considered statistically significant (GraphPad Prism 5.0; GraphPad Software, CA). The unpaired t-test show a statistically significant difference in tumor growth between the CIMO treated and control groups (p value=0.0385 as compared to DMSO treated control group).

The effect of CIMO on constitutive phospho-STAT3 levels in HCC tumor tissues is further analyzed by immunohistochemical analysis. Solid tumors from control and drug-treated groups are fixed with 10% phosphate buffered formalin, processed, and embedded in paraffin. The sections are cut to 5 micron size and deparafinized in xylene, dehydrated in graded alcohol, and finally hydrated in water. Antigen retrieval is conducted by boiling the slide in 10 mM sodium citrate (pH 6.0) for about 30 minutes. Immunohistochemistry is conducted following the manufacturer's instructions (Dako LSAB Kit). Briefly, endogenous peroxidases are quenched with 3% hydrogen peroxide. Sections are incubated with primary antibodies for about 2 hours as follows: anti-pSTAT3, anti-Ki-67 and anti-caspase-3 (each at 1:100 dilutions). The slides are subsequently washed several times in TBS with 0.1% Tween-20 and are incubated with biotinylated linker for about 45 minutes, provided in the LSAB Kit according to the manufacturer's instructions. Immunoreactive species are detected using 3, 3'-diaminobenzidine tetrahydrochloride as a substrate. The sections are counterstained with Gill's hematoxylin and mounted under glass cover slips. Images are taken using an Olympus BX51 microscope (magnification, 40x). Quantitative analysis of immunohistochemistry images are done by visual scores between the control and treated images. In this expression quantitation technique, each image is divided into four parts and each part is individually quantitated for the biomarker expression. A cell scored as positive refers to the presence of brown staining (peroxidase) in any part of the studied tissue. A negative cell scored refers to no staining or weak staining.

Based on immunohistochemical analysis, it is found that CIMO significantly inhibits constitutive STAT3 activation in treated vs. control group (FIG. 6B). The effect of CIMO is also analyzed on the expression of Ki-67 (marker of proliferation) and cleaved caspase-3 (marker of apoptosis). As shown in FIG. 7, expression of Ki-67 is downregulated and that of cleaved caspase-3 is significantly increased in CIMO-treated group, when compared with control.

Example 15

In Silico Interaction of Compound 1 (CIMO) Towards with the Kinase Domain of JAK2

In order to better understand compound action on a mechanistic level, computational studies are performed. In this study, CIMO shows potent anti-cancer activity via. the inhibition of JAK2-STAT3 pathway, and hence the possibility that CIMO interacts with the kinase domain of JAK2 directly is considered. Therefore, the JAK2 inhibitor: 1-methyl-1H-imidazole which modulates JAK/STAT pathway is considered for the present study. A molecular docking study is carried out to examine the possibility of CIMO in binding to the kinase domain of JAK2. The docking scores (DS) of the biologically active ligands with the kinase domain of JAK2 (PDB ID: 4C61) are summarized (FIG. 8A). Based on Ligand Fit DS calculations, CIMO shows a docking score of 95.07 kcal/mol, which is higher when compared to other known structurally related compounds (Table 4). The known STAT3 inhibitors such as Stattic and staurosporine bind to the kinase domain of JAK2 with predicted binding energies of 37.2 and 83.2 kcal/mol respectively, thus establishing better efficiency of CIMO which shows a higher docking score. FIG. 8 shows the best docked pose of CIMO as defined by the highest DOCK score. The protein-ligand interactions as shown in FIG. 8C have been classified into four clusters in order to enable identification and comparison of interaction patterns of CIMO moieties with specific JAK2 residues across other known JAK2 inhibitors. In cluster 1, the interaction of cyano-biphenyl moiety of CIMO bound to the hydrophobic pocket comprising of Leu855, Gly856, Ala880, Met929, Val863, Leu932, and Gly935 is seen. In cluster II, the indole moiety interaction with Gly993, Asp994, Gly882, and Ser862 is observed. In cluster III, the cyclohexyl attached azaspirane moiety of CIMO binds to Gly996, Leu997, Glu898, Phe895, Gly861, and Leu884. In addition, the methoxy phenyl moeity of CIMO interacts with Asp894, His891, and Glu890. These results establish that CIMO binds strongly to the kinase domain of JAK2, thereby mediating the inhibition of JAK-STAT pathway and the subsequent anti-cancer effect.

TABLE 4

Computational analysis of the binding of various compounds towards the kinase domain of JAK2

| Compounds | LS1D | LS2D | −PLP1 | −PLP2 | JAIN | −PMF | DS |
| --- | --- | --- | --- | --- | --- | --- | --- |
| CIMO | 4.14 | 6.24 | 87.72 | 78.9 | 0.26 | 125.12 | 95.07 |
| 5 g | 2.65 | 6.67 | 93.26 | 84.61 | −0.45 | 90.87 | 84.8 |
| Staurosporin | 2.14 | 7.16 | 91.3 | 85.7 | −0.57 | 91.4 | 83.2 |
| Stattic | 6.1 | 12.8 | 45.1 | 34.5 | 2.0 | 65.6 | 37.2 |

While considerable emphasis has been placed herein on the particular features of this disclosure, it will be appreciated that various modifications can be made, and that many changes can be made in the preferred embodiments without departing from the principles of the disclosure. These and other modifications in the nature of the disclosure or the preferred embodiments will be apparent to those skilled in the art from the disclosure herein, whereby it is to be distinctly understood that the foregoing descriptive matter is to be interpreted merely as illustrative of the disclosure and not as a limitation.

We claim:

1. A compound of Formula I

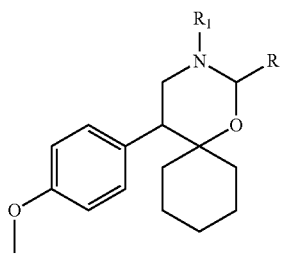

Formula I where, 'R' is selected from a group consisting of 1-(4-(2-cyanophenyl)1-benzyl-1H-indol-3-yl, 2-butyl-5-chloro-3-(4-benzyloxy-1-benzyl)-imidazol-4-yl, 2,6-dichlorophenyl and chromene-4-one;

'$R_1$' is hydrogen or 4-(2-cyanophenyl)benzyl;

or its tautomers, isomers, or salts thereof.

2. The compound as claimed in claim 1, wherein said compound is selected from a group comprising:
2-(1-(4-(2-cyanophenyl)1-benzyl-1H-indol-3-yl)-5-(4-methoxy-phenyl)-1-oxa-3-aza spiro(5,5) undecane;
2-(2-butyl-5-chloro-3-(4-benzyloxy-1-benzyl)-imidazol-4-yl)-5-(4-methoxy-phenyl)-1-oxa-3-aza spiro(5, 5) undecane;
3-[5-(4-Methoxy-phenyl)-1-oxa-3-aza-spiro[5.5]undec-2-yl]-chromen-4-one;
2-(2,6-dichlorophenyl)-5-(4-methoxy-phenyl)-1-oxa-3-(4-(2-cyanophenyl)benzyl azaspiro(5,5) undecane.

3. The compound as claimed in claim 1, wherein said compound is crystalline and has a melting point ranging from about 55° C. to about 160° C.

4. The compound as claimed in claim 1, wherein said compound is soluble in solvent selected from a group comprising DMSO, CDCl$_3$, methanol, DMF, ethanol and combinations thereof.

5. A method for preparing a compound of Formula I,

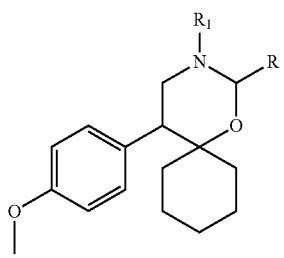

Formula I where, 'R' is selected from a group consisting of 1-(4-(2-cyanophenyl)1-benzyl-1H-indol-3-yl, 2-butyl-5-chloro-3-(4-benzyloxy-1-benzyl)-imidazol-4-yl, 2,6-dichlorophenyl, and chromene-4-one;

'$R_1$' is hydrogen or 4-(2-cyanophenyl)benzyl;

or its tautomers, isomers, or salts thereof;

said method comprising steps of:

a) reacting amino alcohol with an aldehyde in presence of a base to obtain the compound of Formula I wherein '$R_1$' is hydrogen, 'R' is selected from a group consisting of 1-(4-(2-cyanophenyl)1-benzyl-1H-indol-3-yl, 2-butyl-5-chloro-3-(4-benzyloxy-1-benzyl)-imidazol-4-yl, 2,6-dichlorophenyl and chromene-4-one; and b) optionally, reacting the compound of Formula I of step (a) with 4-(2-cyanophenyl) benzyl halide to obtain the compound of Formula I, wherein 'R' is 2,6-dichlorophenyl, and '$R_1$' is 4-(2-cyanophenyl) benzyl moiety.

6. The method as claimed in claim 5, wherein the amino alcohol is 1-(2-amino)-1-(4-methoxy-phenyl-ethyl)-cyclohexanol; the 4-(2-cyanophenyl) benzyl halide is 4-(2-cyanophenyl)benzyl bromide; the base is selected from a group comprising potassium carbonate, sodium carbonate and a combination thereof; and the aldehyde is selected from a group comprising

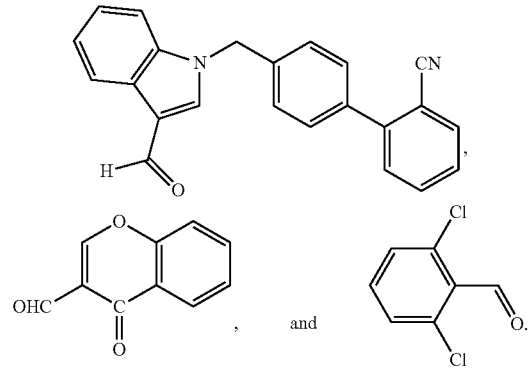

7. The method as claimed in claim 5, wherein the reaction is carried out in a solvent selected from a group comprising methanol, ethanol, DMSO, DMF, Ethyl acetate, Ether and combinations thereof.

8. The method as claimed in claim 5, wherein the reaction is carried out at temperature ranging from about 25° C. to about 30° C.; and for time period ranging from about 4 hours to about 5 hours.

9. The method as claimed in claim 5, wherein the compound of Formula I is extracted, dried and re-crystallized.

10. A method of inhibiting a protein selected from a group comprising tyrosine kinase, Signal Transducer and Activator of Transcription (STAT) and a combination thereof in a cancer cell, said method comprising act of contacting the compound of claim 1 with the cancer cell for inhibiting the protein.

11. The method as claimed in claim 10, wherein the tyrosine kinase is selected from a group comprising Janus kinase 1 (JAK1), Janus kinase 2 (JAK2), c-Src kinase and combinations thereof; and the STAT is Signal Transducer and Activator of Transcription 3 (STAT3).

12. The method as claimed in claim 10, wherein concentration of the compound of Formula I ranges from about 7.3 μM to about 50 μM.

13. The method as claimed in claim 10, wherein the inhibition of the tyrosine kinase leads to inhibition of STAT3 activation.

14. The method as claimed in claim 13, wherein the inhibition of STAT3 activation is carried out by suppressing STAT3 phosphorylation at tyrosine 705 (Y705) residue.

15. The method as claimed in claim 14, wherein the phosphorylation is selected from a group comprising constitutive phosphorylation, interleukin-6 (IL-6) induced phosphorylation and a combination thereof; and the constitutive phosphorylation is regulated by tyrosine kinase.

16. The method as claimed in claim 13, wherein inhibition of STAT3 activation result in reduction in nuclear localization of STAT3 in cancer cell.

17. The method as claimed in claim 10, wherein said method inhibits Janus kinase—Signal Transducer and Activator of Transcription (JAK-STAT) pathway in the cancer cell.

18. The method as claimed in claim 10, wherein said method treats cancer; and the cancer is selected from a group comprising hepatocellular carcinoma (HCC), leukemia, lymphoma, prostate cancer, breast cancer, ovarian cancer, multiple myeloma, head and neck cancer, gastric cancer and combinations thereof.

* * * * *